United States Patent
Sekhar

(10) Patent No.: US 9,084,760 B2
(45) Date of Patent: *Jul. 21, 2015

(54) INCREASING GLUTATHIONE LEVELS FOR THERAPY

(71) Applicant: Baylor College of Medicine, Houston, TX (US)

(72) Inventor: Rajagopal V. Sekhar, Missouri City, TX (US)

(73) Assignee: Baylor College of Medicine, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/278,771

(22) Filed: May 15, 2014

(65) Prior Publication Data

US 2014/0288177 A1 Sep. 25, 2014

Related U.S. Application Data

(63) Continuation of application No. 13/728,903, filed on Dec. 27, 2012, now Pat. No. 8,802,730, which is a continuation of application No. 12/641,894, filed on Dec. 18, 2009, now Pat. No. 8,362,080.

(60) Provisional application No. 61/138,591, filed on Dec. 18, 2008.

(51) Int. Cl.
*A61K 31/195* (2006.01)
*A61K 31/198* (2006.01)

(52) U.S. Cl.
CPC .................... *A61K 31/198* (2013.01)

(58) Field of Classification Search
USPC ........................................ 514/562
See application file for complete search history.

(56) References Cited

U.S. PATENT DOCUMENTS

| | | | |
|---|---|---|---|
| 5,719,302 A | 2/1998 | Perrut et al. | |
| 5,945,318 A | 8/1999 | Breivik et al. | |
| 6,204,401 B1 | 3/2001 | Perrut et al. | |
| 6,518,049 B1 | 2/2003 | Haraldsson et al. | |
| 6,630,188 B1 | 10/2003 | Breivik et al. | |
| 7,799,782 B2 * | 9/2010 | Munson et al. | 514/234.5 |
| 8,362,080 B2 * | 1/2013 | Sekhar | 514/562 |
| 8,802,730 B2 * | 8/2014 | Sekhar | 514/562 |
| 2007/0191467 A1 | 8/2007 | Rongen et al. | |
| 2008/0085911 A1 | 4/2008 | Rongen et al. | |
| 2008/0125490 A1 | 5/2008 | Svensson et al. | |

OTHER PUBLICATIONS

"LOVAZA," located on www.lovaza.com website, downloaded on Nov. 12, 2008.
"What are the Benefits of LOVAZA?" located on www.lovaza.com website, downloaded on Nov. 12, 2008.
Guthikonda et al., "The Effect of Aging on Glutathione Synthesis and Oxidative Stress," Poster, American Geriatrics Society Annual Scientific Meeting, 2006.
Guthikonda et al., "The Effect of Aging on Glutathione Synthesis and Oxidative Stress," Poster, Baylor College of Medicine, Graduate Student Symposium, 2006.
Guthikonda et al., "The Effect of Diabetes on Glutathione Synthesis and Oxidative Stress," Poster, American Diabetes Association Scientific Sessions, 2006.
Patel, "The Role of Glutathione on Fat Oxidation, Weight Regulation and Insulin Resistance with Aging," Poster, Baylor College of Medicine, Graduate Student Symposium, Apr. 2008.

* cited by examiner

*Primary Examiner* — Rei-Tsang Shiao
(74) *Attorney, Agent, or Firm* — Norton Rose Fulbright US LLP

(57) ABSTRACT

The present invention concerns compositions and methods related to utilizing glycine and N-acetylcysteine for a variety of methods, including, for example, reducing deleterious effects of oxidative stress; treating and/or preventing diabetes; and/or increasing GSH levels.

6 Claims, 49 Drawing Sheets

A

B

A

B

Table 3: Oxidant concentrations in all subjects
DM = Diabetes mellitus
[a] Non-DM controls vs DM subjects: Pre-supplementation
[b] DM subjects: Pre-supplementation vs Post-supplementation
[c] DM subjects: Post-supplementation vs Non-DM controls

| Parameters | Non-DM Controls | DM-Pre | DM-post | P |
|---|---|---|---|---|
| DROMs (U.Carr) | 286 ± 10 | 403 ± 11[a] | 369 ± 10[b,c] | [a]<0.00001, [b]<0.05, [c]<0.0001 |
| Lipid Peroxide (umol/L) | 2.6 ± 0.4 | 10.8 ± 1.2[a] | 6.2 ± 0.9[b,c] | [a]<0.0001, [b]<0.01, [c]<0.05 |

FIG. 46

INCREASING GLUTATHIONE LEVELS FOR THERAPY

The present application is a continuation of U.S. patent application Ser. No. 13/641,894, filed Dec. 27, 2012, which is a continuation U.S. patent application Ser. No. 12/641,894, filed Dec. 18, 2009, now U.S. Pat. No. 8,362,080, issued Jan. 29, 2013, which claims priority to U.S. Provisional Patent Application Ser. No. 61/138,591, filed Dec. 18, 2008, all of which applications are incorporated by reference herein in their entirety.

FIELD OF THE INVENTION

The present invention is directed to the fields of biochemistry, cell biology, chemistry, molecular biology, and medicine.

BACKGROUND OF THE INVENTION

The free radical theory of aging suggests that the biological process of aging results in increased oxidative stress in elderly humans. The ability of a cell to resist the damaging potential of oxidative stress is determined by a vital balance between generation of oxidant free radicals and the defensive array of antioxidants available to the cell. There are multiple antioxidant defense systems and of these, glutathione (GSH) is the most abundant intracellular component of overall antioxidant defenses. GSH, a tripeptide, is synthesized from precursor amino-acids glutamate, cysteine, and glycine in two steps catalyzed by glutamate cysteine ligase (GCL, also known as γ-glutamylcysteine synthetase, EC 6.3.2.2) and γ-L-glutamyl-L-cysteine:glycine ligase (also known as glutathione synthetase, EC 6.3.2.3), and GSH synthesis occurs de novo in cells.

Glutathione deficiency has been implicated in several diseases in humans including protein energy malnutrition in children, sickle-cell anemia, infection, neurological disorders such as Parkinson's disease, HIV infections, liver disease and cystic fibrosis. Evidence from several animal (Stohs et al., 1984; Farooqui et al, 1987; Liu et al., 2000) and human studies (Al-Turk et al., 1987; Matsubara et al., 1991; Lang et a., 1992; Samiec et al., 1998; Erden-Inal et al., 2002; Loguercio et al., 1996) suggest that concentrations of glutathione also decline with aging. GSH deficiency in aging is associated with an increased pro-oxidizing shift (Rebrin, 2008) leading to increased oxidative stress (Rikans and Hornbrook, 1997). These changes have been implicated in diseases of aging such as cataracts (Campisi et al., 1999; Castorina et al., 1992; Sweeney et al., 1998), age-related macular degeneration (Samiec, 1998), altered immune function (Fidelus and Tsan, 1987; Furukawa et al., 1987) and neurodegenerative disease (Liu et al., 2004), and in increased DNA damage (Hashimoto et al., 2008) at a molecular level. While the underlying mechanisms for aging-associated glutathione deficiency is not well understood, there are suggestions that perturbations in glutathione synthesis could be involved (Toroser and Sohal, 2007).

Two key mechanisms for the intracellular GSH deficiency are suppressed synthesis and/or increased consumption relative to synthetic capacity. To determine whether increased GSH consumption or suppressed synthesis was responsible for intracellular GSH deficiency in aging, the inventor used an established stable-isotope tracer method (Reid and Jahoor, 2000) to measure in vivo erythrocyte GSH synthesis in 8 young and 8 aged humans, before and after 14 days of supplementation of 2 key amino-acid precursors of glutathione synthesis, cysteine and glycine. Glutathione concentrations within erythrocytes, and oxidative stress and markers of oxidant damage within plasma, were also measured.

Other and further objects, features, and advantages will be apparent from the following description of the presently preferred embodiments of the invention, which are given for the purpose of disclosure.

SUMMARY OF THE INVENTION

In certain embodiments of the invention, the present invention concerns compositions and methods related to utilizing glycine and n-acetylcysteine (NAC) for therapeutic and/or preventative indications in mammals in need thereof. The mammals can be of any kind and can include humans, dogs, cats, horses, pigs, sheep, and goats, for example. In certain embodiments, the present invention is directed to one or more methods and/or compositions that concern impaired glutathione turnover and/or increased oxidative stress and/or oxidant damage in a mammal, including such impaired glutathione turnover and/or increased oxidative stress and/or oxidant damage in aging or diabetes. In specific embodiments, the present invention concerns beneficial effects of dietary supplements with glycine and n-acetylcysteine in a mammal in need thereof, including one that is aging or has diabetes, for example.

A mammal in need thereof can include one that needs prevention or treatment of deleterious effects of aging or that needs prevention or treatment of diabetes or complications from diabetes or that needs prevention or treatment from one or more of the following: dyslipidemia; insulin resistance; obesity; fatty acid oxidation; diabetic dyslipidemia; diabetic microvascular complications (for example, nephropathy, retinopathy, and/or neuropathy); high cholesterol and/or triglyceride levels; fatty liver disease; neurodegenerative disease in aging; statin-induced myopathy.

In some embodiments, the present invention concerns individuals, for example elderly humans, that have decreased GSH levels for any reason, including because of diminished synthesis, and in certain embodiments it is diminished because of poor availability of precursor amino acids, for example. The low GSH state predisposes an individual to increased oxidative stress, measured by plasma markers of oxidative damage, for example. Dietary supplementation with both NAC and glycine results in improved GSH synthesis and concentrations, and decreases in plasma markers of damage, in certain embodiments of the invention.

In one embodiment of the invention, there are methods and compositions that are useful for reducing and/or preventing oxidative stress in an individual. In a specific embodiment, the methods and compositions are useful for treating and/or preventing medical conditions associated with oxidative stress. In a particular embodiment, the methods and compositions of the invention are useful for treating and/or preventing medical conditions associated with reduced levels of glutathione. In one specific embodiment of the invention, the methods and compositions are useful for treating diabetes. In a certain aspect of the invention, the methods and compositions are useful for providing to the elderly. In particular cases, the present invention provides methods and compositions useful for aging.

In certain embodiments, the invention concerns compositions and the following exemplary method(s): method to reduce plasma F2-isoprostane levels; method to reduce plasma F3-isoprostane and/or F2-isoprostane levels (for example, as it relates to a marker for brain oxidative stress); method to increase GSH production; method to increase GSH intracellular concentration; method to increase liver (and separately, muscle, for example) GSH levels; method to improve insulin sensitivity; method to increase fat oxidation; method to reduce body weight; method to treat/prevent dyslipidemia; method to treat/prevent fatty liver disease; method to lower cholesterol level; method of preventing myopathy, including statin induced myopathy; and/or method to lower triglyceride level.

In particular embodiments, the present invention concerns improving at least one symptom of, treating, and/or preventing the following: 1. dyslipidemia and insulin resistance; 2. obesity; 3. fatty acid oxidation; 4. diabetic dyslipidemia; 5. diabetic microvascular complications—nephropathy, retinopathy, neuropathy; 6. lowering cholesterol and triglyceride levels; 7. fatty liver disease; 8. neurodegenerative disease in aging; and/or 9. preventing statin-induced myopathy.

In one embodiment of the invention, there is a composition consisting essentially of glycine and N-acetylcysteine. In another embodiment of the invention, there is a composition consisting of glycine and n-acetylcysteine.

In certain embodiments of the invention, there is a method of reducing deleterious effects of oxidative stress in an individual, comprising the steps of providing an effective amount of glycine and N-acetylcysteine to the individual. In a specific embodiment, the individual is receiving treatment or has received treatment for diabetes.

In an additional embodiment, there is a method of treating and/or preventing diabetes in an individual, comprising the step of providing an effective amount of glycine and n-acetylcysteine to the individual. In specific cases of any aspect of the invention, the glycine and n-acetylcysteine are provided to the individual in the same composition or different compositions. In some specific cases, the glycine and n-acetylcysteine are provided orally to the individual. In particular cases the glycine and n-acetylcysteine are provided to the individual in specific ratio and/or by specific delivery regimen.

In one embodiment of the invention, there is a method of treating and/or preventing diabetes in an individual, comprising the steps of: a) identifying an individual in need of diabetic treatment; and b) providing an effective amount of glycine and N-acetylcysteine to the individual. In a particular embodiment of the invention, there is a method of treating and/or preventing complications from diabetes in an individual, comprising the steps of: a) identifying an individual in need of preventing complications from diabetes; and b) providing an effective amount of glycine and N-acetylcysteine to the individual.

In specific cases of the invention, there is a method of reducing plasma F2-isoprostane levels, F3-isoprostane levels, or both in an individual, comprising the step of providing an effective amount of glycine and n-acetylcysteine to the individual.

In certain aspects, there is a method of increasing GSH production in an individual, comprising the step of providing an effective amount of glycine and n-acetylcysteine to the individual.

In particular aspects, there is a method of increasing GSH intracellular concentration in an individual; increasing liver and/or muscle GSH levels in an individual; improving insulin sensitivity in an individual; increasing fat oxidation in an individual; reducing body weight in an individual; treating and/or preventing dyslipidemia in an individual; treating and/or preventing fatty liver disease in an individual; lowering cholesterol level in an individual; preventing myopathy in an individual and/or lowering triglyceride level in an individual, comprising the step of providing an effective amount of glycine and n-acetylcysteine to the individual.

In certain embodiments of the invention, because aging is associated with impaired fat oxidation and obesity, and also with glutathione deficiency due to impaired synthesis, providing glycine and n-acetylcysteine restores glutathione synthesis and concentrations, and also improves fat oxidation, insulin resistance, obesity, and/or dyslipidemia.

In certain embodiments of the invention, an effective amount of glycine and n-acetylcysteine is provided to an individual for the improved biogenesis and/or mitochondrial function. In specific cases, an effective amount of glycine and n-acetylcysteine is provided to an individual for improving physical performance in the individual, such as improved athletic performance. In certain aspects, the improved mitochondrial biogenesis in the individual directly or indirectly results in improved athletic performance of the individual.

In certain embodiments of the invention, longevity is increased in an individual that is provided an effective amount of glycine and n-acetylcysteine. Thus, in particular embodiments of the invention there are methods and compositions related to increasing lifespan of an individual. The individual may or may not have life-threatening medical conditions. The individual has diabetes or obesity or other medical conditions described herein, in certain embodiments.

In certain cases of the invention, providing an effective amount of glycine and n-acetylcysteine improves PGC1a and/or AMPK levels. In specific cases, such an improvement provides therapeutic benefit in applications related to insufficient levels of PGC1a and/or AMPK.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 46 demonstrates oxidative stress and oxidant damage in treated diabetic and nondiabetic humans.

DETAILED DESCRIPTION OF THE INVENTION

I. Definitions

Figures 1A, 1B:
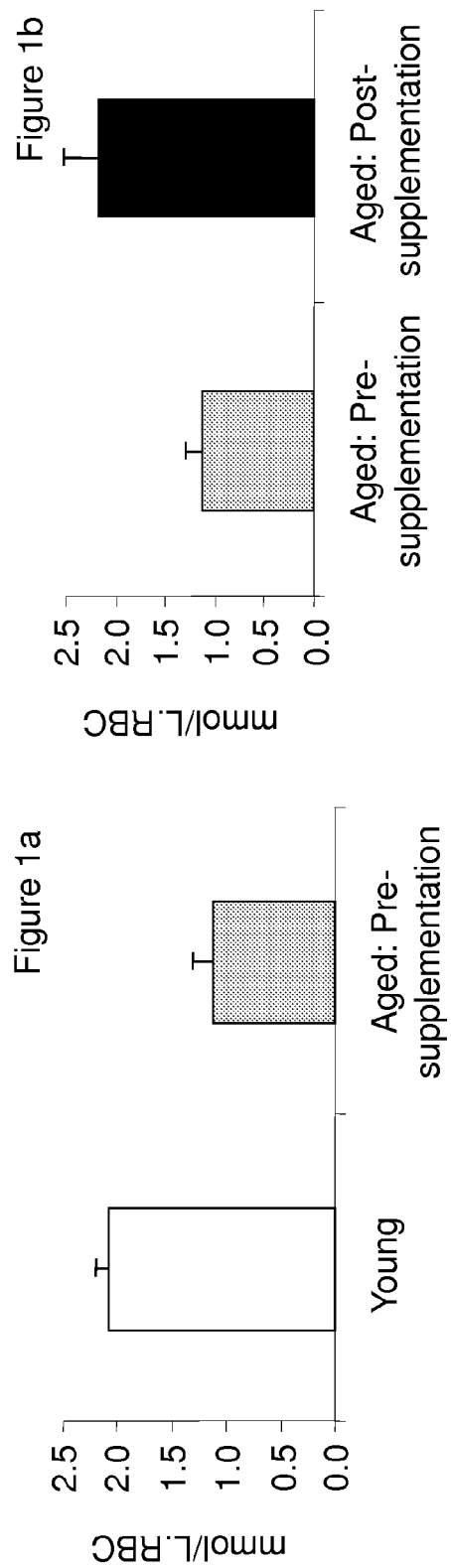
FIGS. 1A-1B show erythrocyte GSH concentrations.

As used herein the specification, "a" or "an" may mean one or more. As used herein in the claim(s), when used in conjunction with the word "comprising", the words "a" or "an" may mean one or more than one. As used herein "another" may mean at least a second or more.

As used herein, the term "complications from diabetes" in specific embodiments refers to diabetic nephropathy, neuropathy, retinopathy, diabetic obesity, diabetic dyslipidemia, cardiometabolic syndrome, and combinations thereof, for example.

As used herein, the term "effective amount" refers to an amount of glycine and n-acetylcysteine that is required to improve at least one symptom of a medical condition in an individual; in specific embodiments, the medical condition exists in the individual directly or indirectly because of insufficient levels of glutathione. In specific embodiments, the effective amount refers to the amount of glycine and n-acetylcysteine that is utilized to increase glutathione levels in the individual.

As used herein, the term "elderly" refers to an individual over the age of at least 60 years of age.

As used herein, the term "oxidative stress" refers to the state in an individual, or cell or tissue of an individual, of an imbalance between the production of reactive oxygen and the ability to detoxify the reactive intermediates or easily repair the resulting damage in a biological system. The natural reducing environment within cells is maintained by processes using a constant input of metabolic energy, and disturbances in this normal redox state can result in toxic effects through the production of, for example, free radicals and peroxides that damage cellular components, such as proteins, lipids, and/or DNA, for example.

II. Certain Embodiments of the Present Invention

In certain embodiments of the invention, there are methods and compositions for the treatment of medical conditions caused directly or indirectly by insufficient GSH levels in the individual. The individual may be of any age or state of health, although in particular embodiments the individual is elderly, is susceptible to particular medical conditions associated directly or indirectly with insufficient GSH levels, or has a medical condition that is associated directly or indirectly with insufficient GSH levels. The compositions delivered to the individual in such cases include at least glycine and n-acetylcysteine, in particular as precursor amino acids to facilitate raising glutathione levels in the individual In some aspects of the invention, an individual is treated for deleterious effects of aging. Aging and certain medical conditions are associated with increased oxidative stress, but the underlying mechanisms are unknown. In certain aspects of the invention, in vivo kinetics of GSH were measured to evaluate whether changes in glutathione turnover could account for the elevated oxidative stress in aging, and whether stimulating glutathione synthesis using dietary amino acid precursors could reduce aging-associated oxidative stress. In exemplary cases, the inventor used a primed infusion of $[^2H_2]$ glycine to measure intracellular GSH synthesis in vivo in 8 non-diabetic elderly humans and 8 healthy controls. The elderly subjects were studied a second time after 2-weeks of dietary supplementation with n-acetylcysteine (as a cysteine donor) and glycine, as GSH precursors. Plasma oxidative stress, markers of oxidant damage, and dietary intakes of protein were also measured. Compared to young controls, elderly subjects had significantly lower erythrocyte GSH concentrations (83.14±6.43 vs. 43.93±6.21%/d, p<0.001) fractional synthetic rates (2.08±0.12 vs. 1.12±0.18 mmol/L·RBC, p<0.001) and absolute synthetic rates (1.73±0.16 vs. 0.53±0.12 mmol/L·RBC/d, p<0.0001) in the basal state. This was associated with significantly increased plasma markers of oxidative damage and reactive oxygen metabolites (309±vs. 332±303 in the elderly subjects compared to controls. After supplementation there were marked and significant increases in erythrocyte GSH concentrations, fraction and absolute synthetic rates to that of young controls, together with a fall in reactive oxygen metabolites and plasma F2-isoprostanes again to that of young humans. These data indicate that elderly humans are GSH deficient, and that this occurs because of suppressed synthesis. Providing precursor supplements in the diet leads to not only to restoration of GSH concentrations primarily due to an increase in the fractional synthetic rate to that of young humans, but also in a striking reduction in oxidative stress and in oxidant damage to that of young healthy controls.

III. Pharmaceutical Compositions

In particular embodiments, the present invention is directed to pharmaceutical compositions for use in treating and/or preventing deleterious effects of aging, diabetes, complications from diabetes, obesity, dyslipidemia, high cholesterol levels, high triglyceride levels, and so forth. In specific embodiments, glycine is administered at 1.33 mmol/kg/d and NAC is administered at 0.83 mmol/kg/d for a particular period of time. Durations of treatment may last for 1 week, 2 weeks, 3 weeks, one month, two months, three months, four months, five months, six months, one year, two years, five years, ten years, fifteen years, twenty years, twenty-five years, thirty years, and so forth, for example. In some cases the treatment lasts for the remaining life of the individual. In specific embodiments, the administration occurs until no detectable symptoms of the medical condition remain. In specific embodiments, the administration occurs until a detectable improvement of at least one symptom occurs and, in further cases, continues to remain ameliorated.

Where the invention is directed to treating with the compounds of the present invention, administration of the compounds of the invention with a suitable pharmaceutical excipient as necessary can be carried out via any of the accepted modes of administration. The compounds may be comprised in a pharmaceutically acceptable excipient, which may be considered as a molecular entity and/or composition that does not produce an adverse, allergic and/or other untoward reaction when administered to an animal, as appropriate. It includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated.

Thus, administration can be, for example, intravenous, topical, subcutaneous, transcutaneous, intramuscular, oral, intra-joint, parenteral, peritoneal, intranasal, intravesical or by inhalation. Suitable sites of administration thus include, but are not limited to, skin, bronchial, gastrointestinal, anal, vaginal, eye, bladder, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., REMINGTON'S PHARMACEUTICAL SCIENCES, 18TH ED., Mack Publishing Co., Easton, Pa. (1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see Remington's Pharmaceutical Sciences, supra., and similar publications. The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

Stability of the conjugate can be further controlled by chemical alterations, including D amino acid residues in the polypeptide chain as well as other peptidomimetic moieties. Furthermore, stability of the conjugates could also be enhanced by unnatural carbohydrate residues.

The glycine and N-acetylcysteine components may be formulated in a particular ratio. In certain embodiments, the formulation may comprise the components in the following exemplary ratios: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, 1:150, 1:200, 1:300, 1:400, 1:500, 1:600, 1:750, 1:1000, 1:10,000, and so forth, for example. In particular embodiments, the formulation may comprise the components in the following percentages by formulation (either the same or different percentages for each): 1%, 2%, 3%, 4%, 5%, 6%, 7%, 8%, 9%, 10%, 12%, 15%, 20%, 25%, 30%, 40%, 45%, 50%, 55%, 60%, 65%, 70%, 75%, 80%, 85%, 90%, 95%, 97%, or 99%, for example.

IV. Combination Treatments

Alternatively, the treatment of the invention may precede, follow, or both another treatment by intervals ranging from minutes to weeks. In embodiments where the inventive composition and the other agent are applied separately to a cell of the individual, one would generally ensure that a significant period of time did not expire between the time of each delivery, such that the inventive composition and the other agent would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, for example, wherein the inventive treatment is "A" and the secondary agent for the medical condition of the invention as described herein, such as diabetic treatment (for example only), is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the inventive compositions of the present invention to a patient will follow general protocols for the administration of drugs, taking into account the toxicity, if any, of the molecule. It is expected that the treatment cycles would be repeated as necessary. It also is contemplated that various standard therapies, as well as surgical intervention, may be applied in combination with the described therapy.

V. Kits

Therapeutic kits associated with the compositions of the present invention comprise another aspect of the present invention. Such kits will generally contain, in suitable container means, an inventive composition of the present invention. The kit may have a single container means that contains the inventive composition or it may have distinct container means for the inventive composition and other reagents that may be included within such kits.

The components of the kit may be provided as liquid solution(s), or as dried powder(s). When the components are provided in a liquid solution, the liquid solution is an aqueous or non-aqueous solution, with a sterile aqueous or non-aqueous solution being particularly preferred. When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the composition may be placed, and preferably suitably aliquoted. Where a second agent is provided, the kit will also generally contain a second vial or other container into which this agent may be placed. The kits of the present invention will also typically include a means for containing the agent containers in close confinement for commercial sale. Such containers may include injection or blow-molded plastic containers into which the desired vials are retained, for example.

In the kit of the invention, the glycine and the N-acetylcysteine may be provided separately or in a mixture together.

VI. Examples

The following examples are included to demonstrate preferred embodiments of the invention. It should be appreciated by those of skill in the art that the techniques disclosed in the examples which follow present techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

The present example concerns exemplary materials and methods for methods and/or compositions of certain embodiments of the present invention.

Subjects: The study was approved by the Institutional Review Board for Human Studies at Baylor College of Medicine, and the procedures followed were in accordance with the ethical standards of the institution. Ten healthy elderly humans (60-75 years) were recruited into the aged arm, and ten younger subjects (20-40 years) were recruited as young controls. The elderly subjects were free of diabetes mellitus, thyroid disorders, hypercortisolemia, liver or renal impairment, and had had no opportunistic infections or illnesses for 6 months. All had sedentary lifestyles and none consumed unusual diets or dietary supplements.

Subjects had a 4 day habitual diet assessment by a qualified dietitian where they charted and weighed all food consumed over a 4 day period prior to the study.

Subjects had an initial visit to measure blood counts, glucose concentrations, liver and renal profiles.

Metabolic study protocol: Subjects were studied in the adult General Clinical Research Center (GCRC) of Baylor College of Medicine after obtaining written informed consent. The protocol consisted of intravenous infusions of stable isotopes to measure glutathione synthesis in the fasted state, before and after 14 days of dietary supplementation with glutathione precursor amino acids cysteine (as n-acetylcysteine) and glycine. Subjects were asked to consume their usual habitual diets, and avoid any alcohol from one week before beginning the study to the end of the study period. They were fasted for 10 h before the start of the stable isotope infusions.

The primary outcome variables were fractional and absolute synthetic rates of glutathione, plasma F2-isoprostane and lipid peroxide levels, and plasma oxidative stress measured as diacron reactive oxygen metabolites (DROMS).

Stable Isotope protocol: A sterile solution of [$^2H_2$]glycine (Cambridge Isotope Laboratories, Woburn, Mass.) was prepared in saline. On the morning of the infusion day, intravenous catheters were inserted into superficial veins of both arms, one for continuous infusion of the tracer solution and the other for repeated blood sampling. After a 20-ml blood sample prior to infusions was drawn, a bolus intravenous infusion of [$^2H_2$]glycine (20 µmol/kg) was given to prime the glycine pool followed by a constant infusion of the same isotope at the rate of 15 µmol·kg$^{-1}$·h$^{-1}$, and maintained for 8 h. Additional 5-ml blood samples were taken at 4, 5, 6, 7, and 8 h for measurement of erythrocyte GSH-derived glycine isotopic enrichments.

Sample Analyses:

Blood chemistries. Baseline blood samples were collected. The samples for plasma analyses were immediately centrifuged, and plasma separated and frozen in a −80 C freezer for later analyses. Hemoglobin, hemotocrit and red blood cell counts were measured. Oxidative stress was measured using a diacron Reactive Oxygen Metabolites (DROMS) kit. Plasma chemistries, lipid peroxides and F2-isoprostanes were measured as outlined below. An additional tube was collected for measurement of F2 isoprostanes.

Erythrocyte GSH analyses. Erythrocyte GSH concentration and isotopic enrichment were measured in duplicate 1-ml aliquots of whole blood collected. Briefly, one sample was mixed immediately in a cryotube with 0.5 ml of chilled, isotonic monobromobimane (MBB) buffer solution (pH 7.5) containing the following (in mmol/l): 5 MBB, 17.5 Na$_2$EDTA, 50 potassium phosphate, 50 serine, and 50 boric acid. The whole blood-MBB mixture was centrifuged at 1,000 g for 10 min at 4° C., and then the supernatant fluid was incubated in the dark for 20 min for development of the plasma GSH-MBB derivative. Another 1.0 ml of MBB buffer was added to the packed erythrocytes, which were immediately lysed by rapid freeze and thaw with liquid nitrogen, and the lysed erythrocyte-MBB buffer mixture was shaken and left in the dark at room temperature for 20 min for development of the erythrocyte GSH-MBB derivative. Proteins were precipitated by using 0.5 ml of 2 mol/l perchloric acid, and the supernatant fluids were stored at −70° C. until further analysis.

Erythrocyte GSH was isolated and the concentration measured using a Waters HPLC system using a 717plus autosampler complexed to a Waters 2475 fluorescent detector and equipped with a reverse-phase ODS Hypersil column (5 µm, 4.6×200 mm; Waters Inc.,). Elution of the GSH was accomplished with a 3-13.5% acetonitrile linear gradient in 1% acetic acid (pH 4.25) at a flow rate of 1.1 ml/min. The GSH elution was collected using a fraction collector, dried, and hydrolyzed for 4 h in 4 mol/l HCl at 110° C. (REFS).

Erythrocyte free glycine was extracted from the protein-free supernatant by cation exchange chromatography. Erythrocyte free glycine and erythrocyte GSH-derived glycine were converted to the n-propyl ester heptafluorobutyramide derivatives, and the isotope ratio of each was measured by negative chemical ionization gas chromatography mass spectrometry on an Agilent 6980 gas chromatograph complexed to a 5973 mass spectrometer (Agilent Technologies, Wilmington, Del.), monitoring ions at mass to charge ratio (m/z) 293 to 295.

Oxidant stress. The D-ROMS test was used to measure plasma hydroperoxide concentration as an index of free radical formation. This test is based on the concept that the amount of organic hydroperoxides present in plasma is related to the free radicals from which they are formed. Briefly, plasma is reacted with an acidic acetate buffer (pH 4.8), which liberates transition metal ions that catalyze the decomposition of the hydroperoxides to alkoxy and peroxyl radicals. These newly formed radicals in turn oxidize the spectrophotometric marker (N,N-diethyl-p-phenylenediamine), which is detectable at an absorption at 505 nm as U.CARR. (carratelli units). One U.CARR. is equal to 0.8 mg/l, hydrogen peroxide.

Plasma markers of Oxidant damage (F2-isoprostanes and lipid peroxides): F2-Isoprostanes. Blood (4 mL) was collected into a lithium-heparin tube containing indomethacin (15 µmol/L). After centrifugation at 2400 g for 10 min at 4° C. to separate plasma and erythrocytes, aliquots of plasma (1 mL) were transferred to Eppendorf tubes containing butylated hydroxytoluene, at a final concentration of 20 mmol/L. One milliliter of 1 mol/L KOH was added to hydrolyze the plasma sample at 40° C. for 30 min to release bound lipids. Then, 1 mL of 1 mol/L HCl and 2 mL of 100 mmol/L formate buffer (pH 3.0) were added and the sample centrifuged at 2400 g for 10 min; the supernatant then underwent solid-phase extraction with the addition of iPF2 {alpha}-III-d4 as an internal standard. An Oasis HLB extraction cartridge preconditioned with methanol and 10 mmol/L formate buffer (pH 3.0) was used for isoprostane extraction by first washing with 5 mL of the formate buffer followed by 5 mL of acetonitrile-water (15:85 by volume), and then F2-isoprostanes were eluted by washing the cartridge with 2 mL of hexane-ethyl acetate-propan-2-ol (30:65:5 by volume). F2-iPs were then analyzed by gas chromatography-mass spectrometry (GC/MS). After evaporation under nitrogen, the extracted F2-iPs in the samples were incubated with 25 μL of pentafluorobenzyl bromide (100 mL/L in acetone) and 25 μL of N,N-diisopropylethylamine (200 mL/L in acetone) at 60° C. for 10 min. The resulting pentafluorobenzyl ester was incubated with 50 μL of N,O-bis-(trimethylsilyl)trifluoroacetamide and 5 μL of N,N-diisopropylethylamine (200 mL/L in acetone) at 60° C. for 5 min, and dried under nitrogen. The pentafluorobenzyl-trimethylsilyl derivatives were reconstituted in 40 μL of isooctane and the samples analyzed on an Agilent 6890 series gas chromatograph (in NCI mode) coupled to a 5973 mass spectrometer (Agilent Technologies, Wilmington, Del.) using methane as the reagent gas. Chromatography was carried out on an SPB-1701 column (30 m×0.25 mm; film thickness, 0.25 μm; Supelco Inc.) using helium as the carrier gas. Selected ion monitoring was performed to monitor the m/z 569 and 573 for F2-iPs and the internal standard, respectively. Peak identification was based on the comparison of the relative retention indices with the internal standard, and the concentration of F2-iP isomers in the samples was calculated using the ratio of the peak height of m/z 569 to that of m/z 573.

Lipid peroxides. Were measured using a standard kit.

Dietary Assessment

Subjects were issued with a food weighing scale and weighed and maintained a 4-day food diary during the week prior to the infusion experiment with verbal and written instructions to add to their diary every time they ate or drank, describing the food/drink as accurately as possible and weighing accurately the amounts of food consumed. The diary consisted of three weekdays and one weekend day. All of the diaries were completed and collected when the subjects were admitted for the infusion experiments. The diaries were analyzed using Nutritionist Five (San Bruno, Calif.) software, by a trained nutritionist.

Calculations

The fractional synthesis rate of erythrocyte GSH (FSRGSH) per day was calculated according to the precursor-product equation as described below FSRGSH(%/day)=(IR$t7$–IR$t5$)/( IR$rbc$×1200/$t7$–$t5$)

where IRt7–IRt5 is the increase in the isotope ratio of erythrocyte GSH-bound glycine between the fifth and seventh hours of infusion, when the isotope ratio of erythrocyte free glycine, IRrbc, had reached a steady state. The units of FSR are percent per day (%/day).

The absolute synthesis rate (ASR) of erythrocyte GSH per day was calculated as.

ASR=Erythrocyte GSH concentration×FSR

Where FSR is the fractional synthesis rate. The units of ASR are expressed as millimoles per liter per day of packed erythrocyte.

Statistics

Data are expressed as means±SD. Differences in means between the SCD group and the control group were determined using an independent t-test with the Satterthwaite adjustment for unequal variances where appropriate. For variables where the distributions were skewed, the two-sample Wilcoxon test was used. Differences in net tracer-to-tracee ratio between groups at plateau were determined by repeated-measures analysis of variance. Data analysis was performed with the Statmate statistical software, version 8.2, for Windows (Stata, College Station, Tex.). Results were considered to be statistically significant if P<0.05.

Example 2

The Effects of Aging on Glutathione Synthesis and Oxidative Stress Baseline Characteristics By design, the ages of the two groups were different as the study groups were aged subjects (60-75 years) and the control group were young subjects (20-40 years). Younger subjects were lighter and had lower body mass indexes compared with aged subjects. There were no differences between the two groups in hematocrit, hemoglobin concentrations, renal functions or liver enzymes. Both groups were non-diabetic, but aged subjects were more insulin resistant with significantly higher concentrations of fasting glucose and glycosylated hemoglobin (Table 1).

TABLE 1

Baseline clinical, hematological and biochemical characteristics

| Parameters | Young controls | Elderly | P |
|---|---|---|---|
| Age (years) | 39.8 ± 1.0 | 70.3 ± 2.4 | <0.01 |
| Weight | 73.9 ± 2.1 | 82.9 ± 5.4 | NS |
| BMI | 25.7 ± 0.6 | 29.8 ± 1.4 | <0.05 |
| Hb (g/L) | 14.2 ± 0.3 | 13.7 ± 0.3 | NS |
| Hematocrit (%) | 42.4 ± 0.7 | 41.0 ± 0.8 | NS |
| Fasting plasma glucose (mmol/L) | 4.9 ± 0.2 | 5.9 ± 0.3 | <0.05 |
| HbA1c (%) | 5.2 ± 0.1 | 5.7 ± 0.1 | <0.01 |
| BUN (mg/dl) | 13.8 ± 1.0 | 13.1 ± 1.0 | NS |
| Creatinine (mg/dl) | 1.0 ± 0.0 | 0.9 ± 0.1 | NS |
| ALT (U/L) | 22.6 ± 3.2 | 28.1 ± 1.7 | NS |
| AST (U/L) | 28.1 ± 4.4 | 25.8 ± 1.5 | NS |

In the aged group alone, there were no differences in hematologic parameters, renal functions of liver enzymes before and after GSH precursor supplementation (Table 2).

TABLE 2

Serum biochemistry pre- and post- supplementation

| Parameters | Pre-treatment | Post-treatment | P |
|---|---|---|---|
| Hb (g/L) | 13.7 ± 0.3 | 13.8 ± 0.2 | NS |
| Hematocrit (%) | 41.0 ± 0.8 | 41.5 ± 0.6 | NS |
| BUN (mg/dl) | 13.1 ± 1.0 | 13.5 ± 1.1 | NS |
| Creatinine (mg/dl) | 0.9 ± 0.1 | 0.9 ± 0.0 | NS |
| ALT (U/L) | 28.1 ± 1.7 | 28.4 ± 1.4 | NS |
| AST (U/L) | 25.8 ± 1.5 | 25.6 ± 1.2 | NS |

Table 3 demonstrates the oxidant concentrations in all subject.

TABLE 3

Oxidant concentrations in all subjects

| Parameters | Elderly-Pre | Elderly-Post | Young Controls | P |
|---|---|---|---|---|
| DROMs (mmol/L) | 346 ± 6$^\infty$ | 277 ± 20* | 304 ± 16 | *<0.05<br>$^\infty$<0.05 |
| F2 Isoprostane (pg/ml) | 136.3 ± 11.3* | 84.8 ± 11.1$^\infty$ | 97.2 ± 8.3 | *<0.05<br>$^\infty$<0.05 |
| Lipid Peroxide (umol/L) | 5.90 ± 1.01* | 2.95 ± 0.63$^\infty$ | 1.92 ± 0.28 | *<0.01<br>$^\infty$<0.001 |

Figures 2A, 2B:
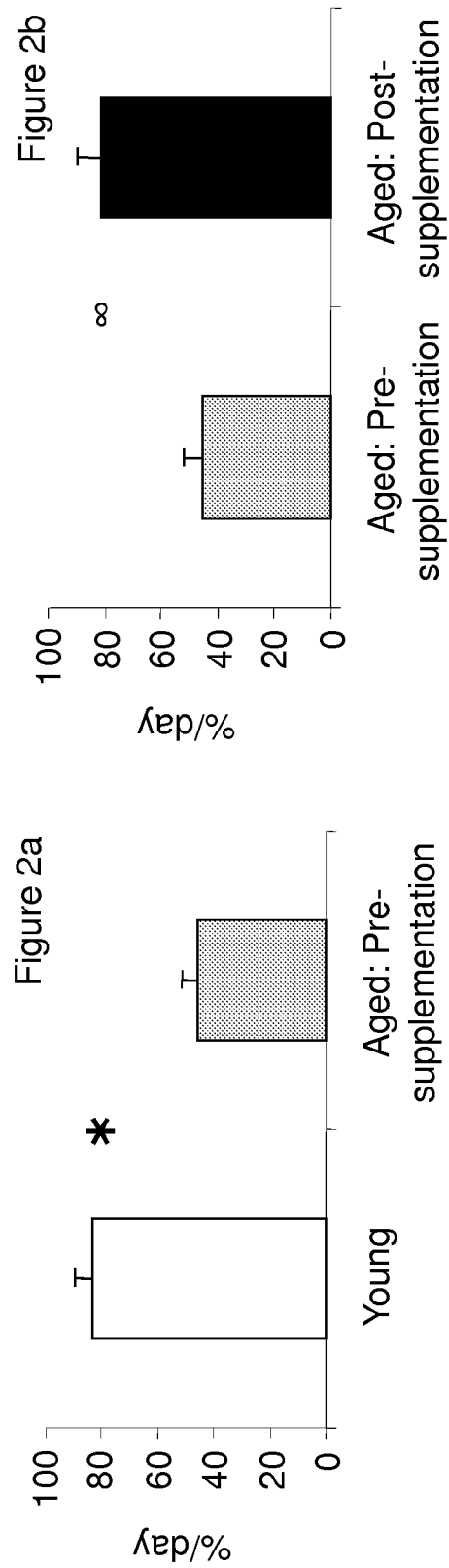
FIGS. 2A-2B show GSH fractional synthesis rate.
Figures 3A, 3B:
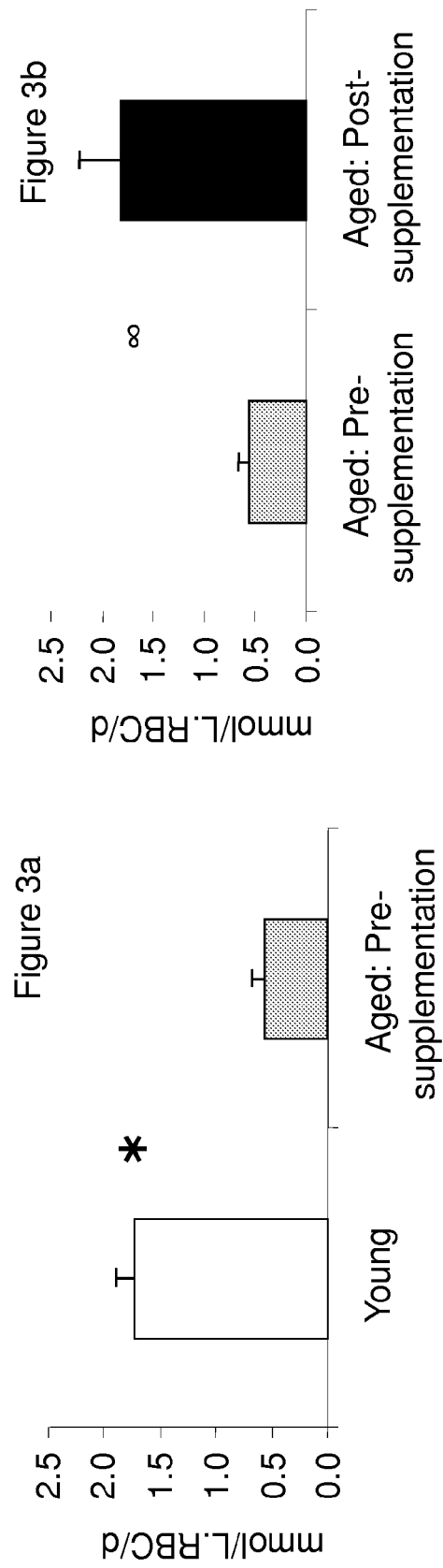
FIGS. 3A-3B show GSH absolute synthesis rate.
Figures 4A, 4B:
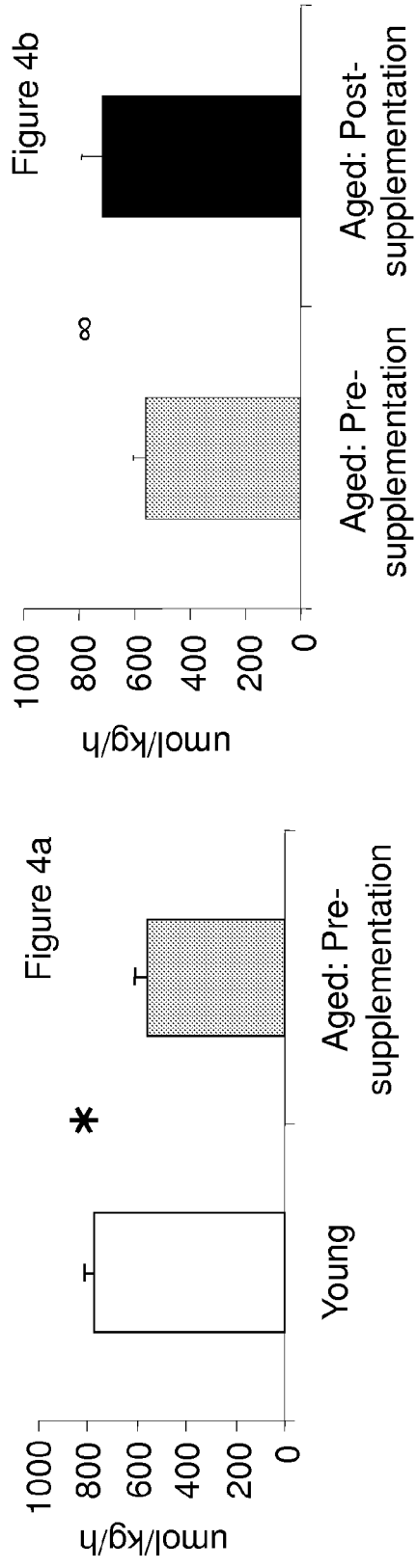
FIGS. 4A-4B show erythrocyte glycine flux.
Figures 5A, 5B:
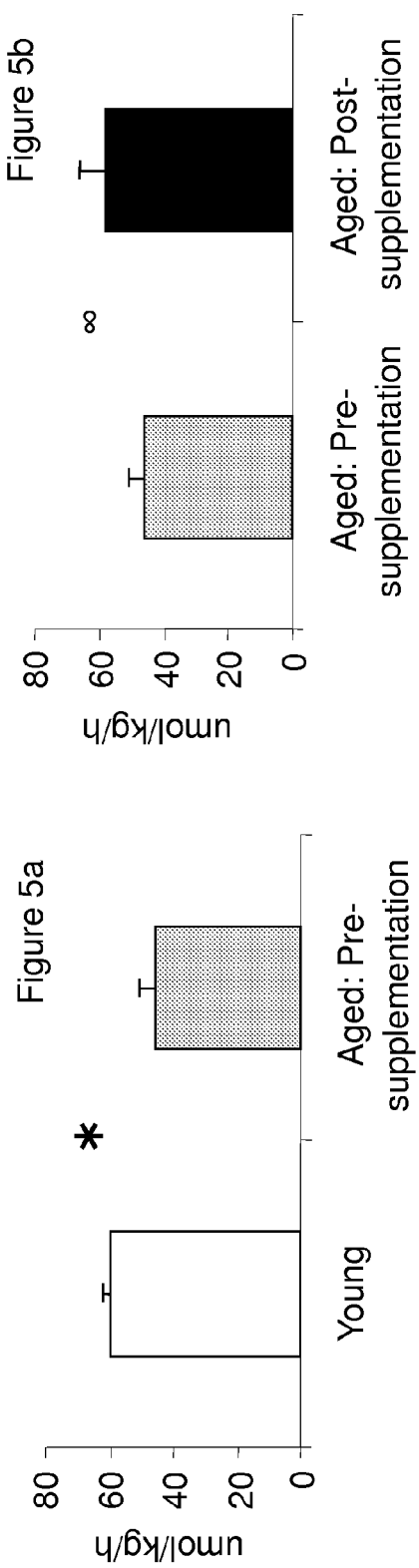
FIGS. 5A-5B show plasma cysteine flux.

*Young controls vs. Aged: Pre-supplementation
$^\infty$Aged: Pre-supplementation vs. Aged: Post-supplementation Erythrocyte and Plasma GSH Kinetics Compared with young controls, aged humans had 46.2% lower erythrocyte GSH concentrations (mean±SE, 1.12±0.18 vs. 2.08±0.12 mmol/L·RBC, P<0.01) (FIG. 1$a$). Aged humans also had 44.9% lower GSH FSR (mean±SE, 45.80±5.69 vs. 83.14±6.43, % day-1, P<0.001), and 68.2% lower ASR (mean±SE, 0.55±0.12 vs. 1.73±0.16, mmol·LRBC-1·day-1, P<0.01), (FIGS. 2$a$ and 3$a$). The erythrocyte glycine flux (mean±SE, 560.0±43.5 vs. 769.1±47.9, umol·kg-1·h-1, P<0.05) and plasma cysteine flux (mean±SE, 46.1±4.5 vs. 59.3±2.4, umol·kg-1·h-1, P<0.05) were also 27.2% and 22.32% lower in the aged humans compared to young controls (FIG. 4$a$).

Supplementation with GSH precursor amino acids cysteine (as n-acetylcysteine) and glycine for 14 days led to 94.6% improvement in erythrocyte GSH concentrations (mean±SE, 1.12±0.18 vs. 2.18±0.35 mmol/L·RBC, P<0.001) and 78.8% higher FSR (mean±SE, 45.80±5.69 vs. 81.91±7.70, % day-1, P<0.001), resulting in 230.9% increase in ASR (mean±SE, 0.55±0.12 vs. 1.82±0.39, mmol·LRBC-1·day-1, P<0.0001). The erythrocyte Glycine flux (mean±SE, 560.0±43.5 vs. 769.1±47.9, umol·kg-1·h-1, P<0.05) increased by 28.1%, and the plasma cysteine flux mean±SE, 46.1±4.5 vs. 59.3±2.4, umol·kg-1·h-1, P<0.05) by 26.7%. There were no significant differences between the young controls and the post supplementation values of any of these parameters, suggesting that in aged humans, these values were restored to those seen in young controls (FIGS. 1-4$b$).

Oxidant Parameters

The lower rates of synthesis of GSH in aged subjects were associated with significantly higher concentrations of markers of oxidative damage (plasma D-ROMs, plasma F2-isoprostanes and lipid peroxides; Table 2), compared to young controls. After 14 days of dietary supplementations, there was a significant fall in these parameters in the aged humans, with no differences between the young group and the GSH-replete aged group post-supplementation.

Significance of Present Exemplary Embodiments

In this study the inventor examined (1) the effect of aging on glutathione synthesis and oxidative stress by comparing in vivo synthesis and concentrations of glutathione within erythrocytes in young and aged humans, plasma oxidative stress and plasma markers of oxidant damage; and (2) the ability of aged humans to correct the defect in GSH synthesis, when their diets were supplemented with GSH precursor proteins for 14 days, and the effect of this improvement on oxidative stress and markers of oxidant damage in the plasma. These data demonstrate that erythrocyte glutathione synthesis and concentrations are markedly reduced in the aged humans compared to younger controls. Glutathione deficiency in aging humans is also associated with an increased oxidant stress and in plasma markers of oxidant damage. When the aged subjects were re-studied after a 14 day period of oral dietary supplementation with two key precursor amino-acids of glutathione synthesis, cysteine (as n-acetylcysteine) and glycine, both the fractional and absolute synthetic rates of glutathione increased to that seen in young controls. This resulted in restoration of erythrocyte glutathione concentrations to that seen in young controls, and also led to significant falls in both oxidative stress and plasma markers of oxidant damage, again to levels found in young controls. These findings indicate that the primary reason for glutathione deficiency in aging humans is diminished synthetic capacity, and predisposes to decreased ability to combat the unopposed increase in oxidative stress, resulting in oxidant damage. The study also demonstrates that the novel use of simple, inexpensive dietary protein precursors to boost glutathione synthesis can both restore glutathione concentrations, and also lower oxidative stress and decrease oxidant damage, in effect restoring the oxidant-antioxidant balance to that observed in young humans.

Several diseases of aging are associated with increased oxidative stress and increased oxidant damage (Samiec et al., 1998), (Campisi et al., 1999; Castorina et al., 1992; Sweeney and Truscott, 1998; Fidelus and Tsan, 1987; Furukawa et al., 1987; Liu et al., 2004) but the underlying mechanisms are not well understood. Although Glutathione is the largest component of intracellular antioxidants, and glutathione deficiency has been reported in aging (Rizvi and Maurya, 2007), to the knowledge of the inventor no prior studies have examined fractional and absolute synthetic rates of glutathione to understand the mechanistic correlation with its intracellular concentrations in aging. One plausible explanation for Glutathione deficiency with aging is abnormalities in protein turnover. Glutathione is a tripeptide comprised of glutamine, cysteine and glycine. As amino acid catabolism and recycling traces its pathway through glutamine as an intermediary, the inventor also examined cysteine and glycine turnover to evaluate decreased GSH synthesis. Compared to younger controls, the turnover rate of glycine within erythrocytes was markedly diminished, and the turnover of cysteine within the plasma was also significantly decreased. This observation is especially interesting as both these amino-acids are 'non-essential' amino acids, and the body retains the ability to synthesize cysteine and glycine, which suggests that protein turnover could be decreased in aging. The process of aging is associated with altered protein turnover (Young, 1990; Boirie et al., 1997; Morais et al., 1997; Fereday et al., 1997; Campbell et al., 1997). In addition, in vivo kinetic studies have shown that when normal adults are fed diets either deficient in sulfur amino-acids (Lyons et al., 2000), or containing reduced amounts of protein (Jackson et al., 2004) GSH turnover is suppressed. Studies in animal models show that absolute dietary deficiencies of GSH precursor amino acids, especially cysteine, can result in decreased GSH concentrations (Grimble et al., 1992; Jahoor et al., 2005; Bella et al., 1999; Cresenzi et al., 2003). Therefore, the available evidence indicates a role for reduced substrate availability to adversely affect in vivo glutathione synthesis with aging, resulting in intracellular glutathione deficiency.

In vivo synthesis of cysteine depends on adequate availability of its precursors, methionine and serine. Methionine is an essential (indispensable) amino acid that is supplied by the diet. Cysteine synthesis occurs primarily in the liver from methionine and serine via the transmethylation-transsulfuration pathway, where methionine is converted to homocysteine, which in turn combines with serine to form cystathionine. The latter is then converted into cysteine and 2-ketobutyrate by cystathionine L-homocysteine lyase. Thus, decreased availability of methionine and serine, impairment of the transmethylation-transsulfuration pathway, and/or deficient dietary intake of cysteine or gastrointestinal malabsorption may lead to cysteine deficiency. In addition, it has also been argued that a non-specific increase of protein intake in aging could lead to unwanted consequences such as hyperhomocystinemia. As homocysteine production is upstream of cysteine, providing n-acetylcysteine directly supplements cysteine without a parallel increase in homocysteine. This study found markedly decreased turnover of both cysteine and glycine in elderly humans, which improved significantly with just 14 days of precursor supplementation.

This constellation of findings indicate that deficiency of GSH precursors predisposes to GSH deficiency, elevated oxidative stress and oxidant damage in aging. To answer the key question of whether supplementing the diets of elderly humans with GSH precursors cysteine and glycine would reverse the age dependent glutathione deficiency, the inventor addressed the same cohort of elderly humans after 14 days of oral dietary supplements. This resulted in significantly increased turnover rates of glycine and cysteine within the erythrocyte and plasma respectively. In turn, there was a significant increase in the fractional synthetic rate and the absolute synthetic rates of GSH, leading to restoration of erythrocyte GSH concentrations to that seen in young controls. The improved GSH synthesis and concentrations led to a dramatic reduction in oxidative stress, and markers of oxidant damage down to the levels observed in the younger controls.

Thus, in particular embodiments of the invention, severe glutathione deficiency underlies the increased oxidative stress and oxidant damage associated with human aging. Glutathione deficiency in aged humans occurs primarily due to a markedly diminished capacity to synthesize glutathione, as a result of limited availability of precursor amino acids cysteine and glycine. Supplementing the diets of at least elderly humans, for example, with these amino-acids for 14 days boosts glutathione synthesis to that seen in young humans and restores intracellular glutathione concentrations, resulting in significant reductions in oxidative stress and oxidant damage.

Example 3

The Effect of Diabetes on Glutathione Synthesis and Oxidative Stress

Increased oxidative stress in poorly controlled diabetes is strongly linked to diabetic complications. Levels of antioxidant Glutathione (GSH) are lower in diabetics, indicative of impaired antioxidant defenses, and associated with increased levels of damaging lipid peroxides (ROOH). The inventor characterized whether (1) GSH concentrations are lower due to decreased GSH synthesis; and (2) dietary supplementation with GSH precursors (cysteine (as NAC) and glycine) would improve GSH synthesis, and decrease plasma markers of oxidative damage (ROOH).

Figure 9:
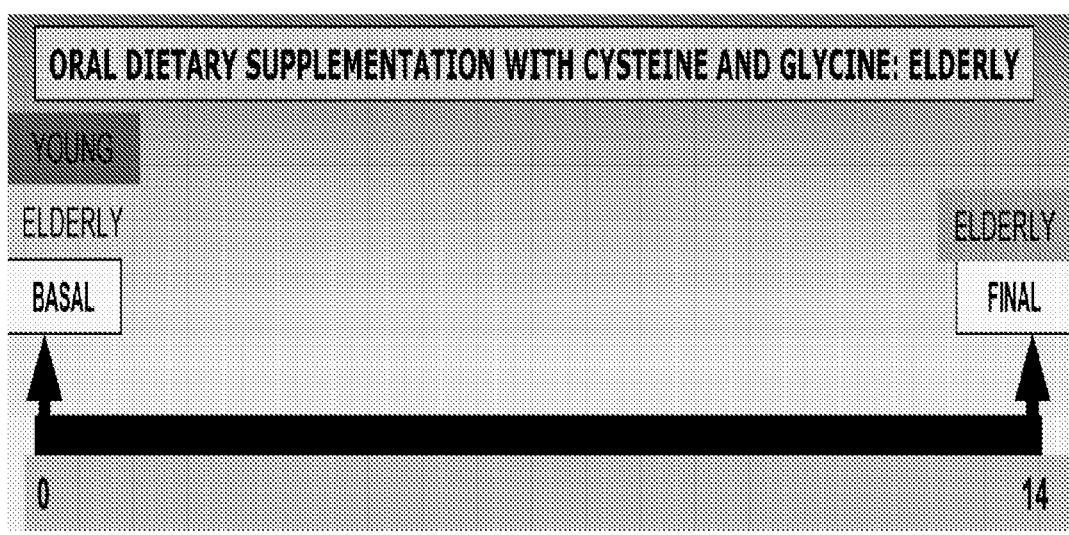
FIG. 9 illustrates an exemplary study design.
Figure 10:
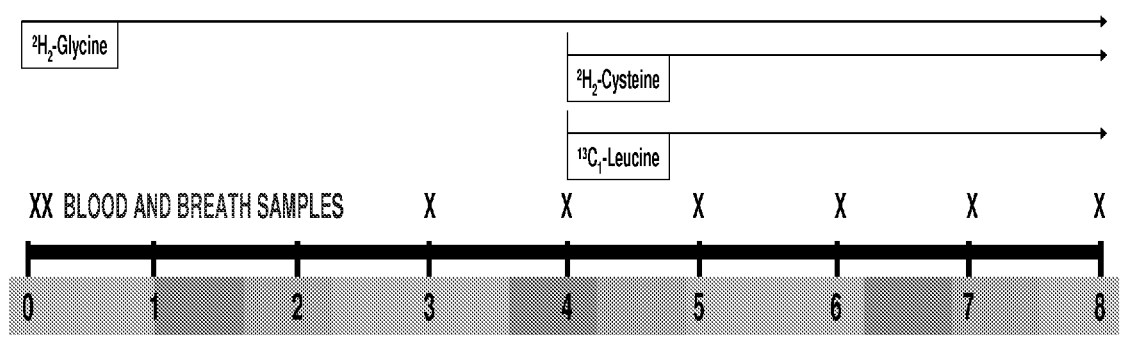
FIG. 10 illustrates an exemplary infusion design.

Eight diabetics were studied before and after 2-week dietary supplementation with either n-acetylcysteine (NAC), glycine, or both. Subjects received infusions of $^2H_2$-glycine to measure the concentration, fractional synthetic rates (FSR) and absolute synthetic rates (ASR) of red cell GSH. Plasma ROOH and glucose levels were measured. Eight non-diabetic subjects were studied as controls. FIG. 9 illustrates an exemplary study design, and FIG. 10 shows an exemplary infusion design.

Results (Mean±SE): Diabetic subjects had a significantly lower GSH concentration (1.17±0.05 v 2.01±0.05 mmol/LRBC, p<0.001), FSR (36±5 v 75±2%/d, p<0.05) and ASR (0.47±0.03 v 1.10±0.06 mmol/L/d, p<0.01) compared to controls. Diabetics had a marked increase in GSH synthesis and concentrations with NAC (concentration 1.17±0.09 v 1.61±0.15, p<0.05; FSR 36±5 v 61±2, p<0.05; ASR 0.47±0.03 v 0.93±0.18, p<0.05), and both supplements (concentrations 1.17±0.05 v 1.76±0.05, p<0.05; FSR 36±5 v 82±12, p<0.05; ASR 0.47±0.03 v 1.20±0.2, p<0.05). ROOH concentrations fell with n-acetylcysteine (13.2±1.7 v 5.78±0.78, p<0.05), and both supplements (13.2±1.7 v 4.65±0.31, p<0.01), and glycemia remained unchanged.

Figure 6:
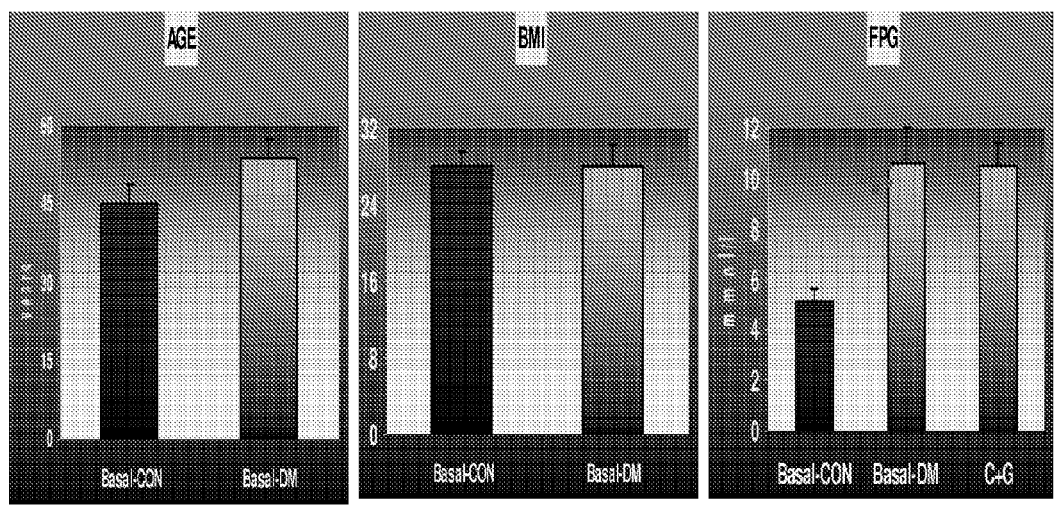
FIG. 6A demonstrates baseline data in diabetec vs. control subjects.
FIG. 6B shows GSH turnover in diabetics after precursor supplementation.
Figure 6:
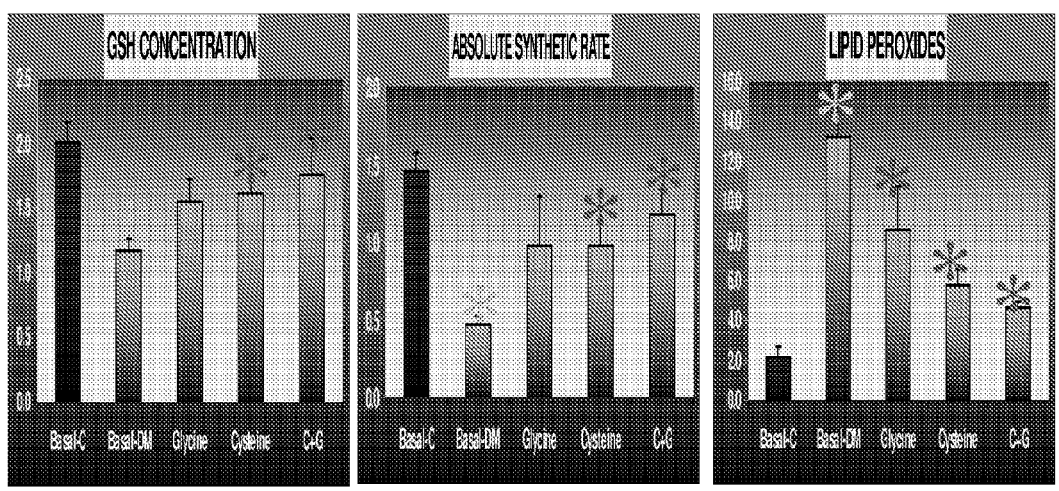
Figure 7:
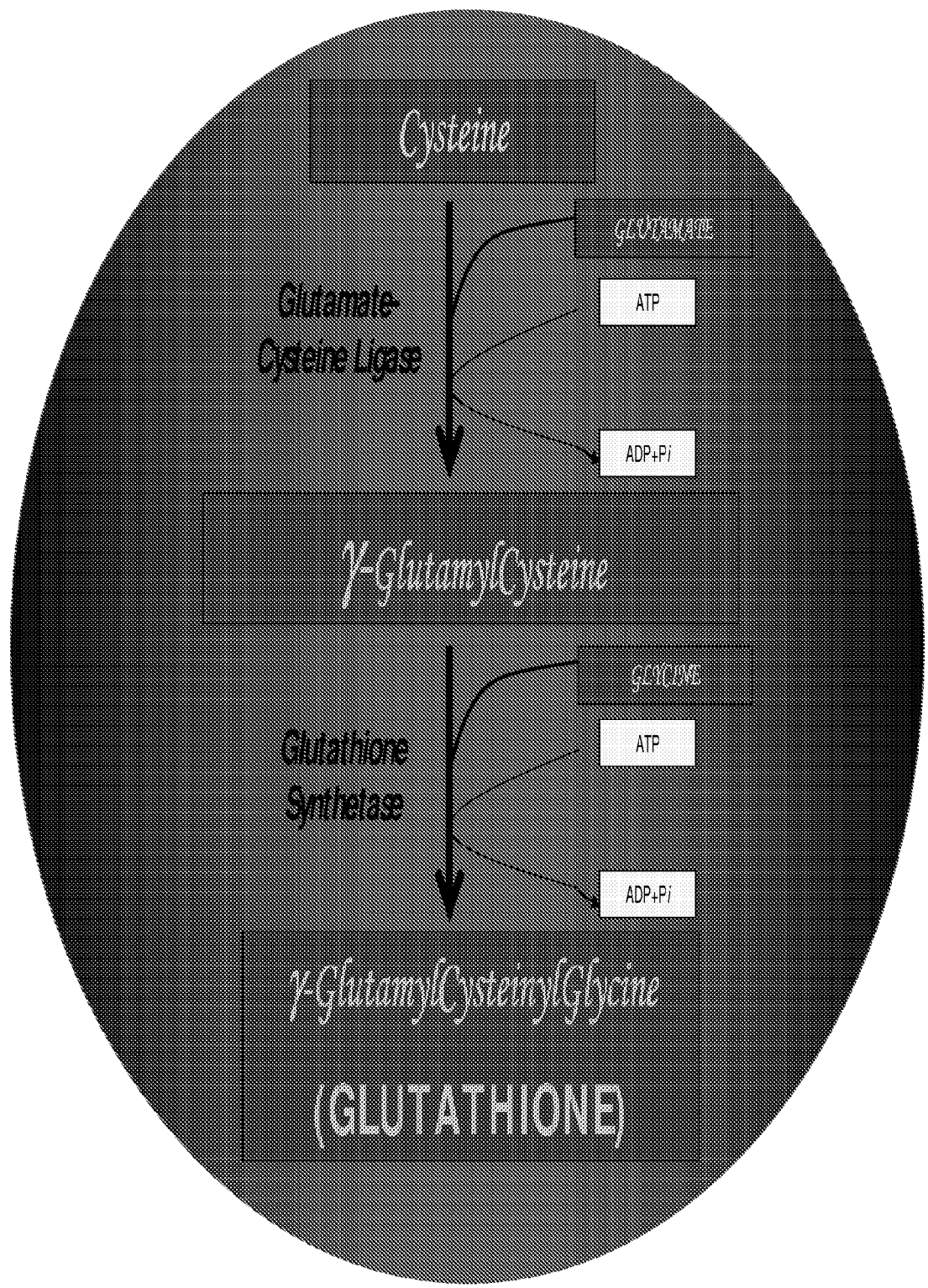
FIG. 7 illustrates a pathway for glutathione synthesis.

FIG. 6A demonstrates baseline data in diabetic vs. control subjects, and FIG. 6B shows GSH turnover in diabetics after precursor supplementation. FIG. 7 illustrates a synthesis pathway for glutathione.

Thus, in particular aspects of the invention, improving glutathione concentrations in hyperglycemic diabetic patients with glycine and NAC supplementation results in a profound decrease in damaging markers of oxidative stress without a change in glycemia. The increased oxidative stress in diabetes is mediated by diminished GSH synthesis, due to limited precursor availability. These findings are useful for the prevention and/or treatment of diabetic complications.

Example 4

Improving GSH Synthetic Rates and Concentrations in the Elderly

Increased oxidative stress with aging has been linked to tissue damage, predisposing to many of the diseases common in the elderly. The glutathione (GSH) redox system is a major component of antioxidant defenses, and levels of protective GSH are lower in the elderly, indicative of impaired antioxidant defenses. Mechanisms responsible for glutathione depletion with aging remain unknown. It was considered that deficiency of precursor amino acids that comprise GSH, namely cysteine and glycine, predispose to decreased GSH synthesis, and oral dietary supplementation with either precursor singly or in combination would augment GSH synthesis, and decrease oxidative stress and plasma markers of ongoing oxidative damage.

Eight nondiabetic elderly humans were studied in the basal state, and after 2-week oral supplementation with either n-acetylcysteine alone, glycine alone, or both supplements, with a 2-week washout period in-between. All subjects received stable isotope infusions of $^2H_2$-glycine and $^2H_2$-cysteine to measure the concentration and the absolute synthetic rate (ASR) of red blood cell GSH. Plasma lipid peroxides were measured as a marker of ongoing damage due to oxidative stress. Eight younger adult subjects were also recruited as controls.

Elderly subjects (69.8±2.1y) had a significantly lower GSH concentration (mmol/L RBC) and ASR (mmol/L/d) compared to younger (40.5±3.4 y) controls (concentrations 1.02±0.2 v 1.73±0.11, p<0.01; ASR 0.57±0.18 v 1.11±0.05, p<0.05). Elderly subjects had a marked increase in glutathione synthesis and concentrations with n-acetylcysteine supplementation, but the greatest response occurred with a combination of both supplements (Basal v post n-acetylcysteine: GSH concentration 1.02±0.24 v 1.37±0.30, p<0.05; GSH-ASR 0.57±0.18 v 0.92±0.23, p<0.05; Basal v post n-acetylcysteine and glycine: GSH-concentrations 1.02±0.24 v 1.53±0.24, p<0.01; GSH-ASR 0.57±0.18 v 1.08±0.11, p<0.05). Concomitantly there was a significant fall in the concentrations of lipid peroxides (mmol/L ROOH) with these supplements (5.10±1.03 v 3.22±1.29, p<0.01, and 5.10±1.03 v 2.65±1.34, p<0.01 for n-acetylcysteine and both supplements respectively). Although the increase in GSH turnover with glycine supplementation alone did not meet statistical significance (Basal v post-glycine: GSH-concentrations 1.02±0.24 v 1.21±0.27; GSH-ASR 0.57±0.18 v 0.71±0.05), this still resulted in a significant fall in ROOH levels (5.10±1.03 v 3.57±1.13, p<0.05).

Figure 8:
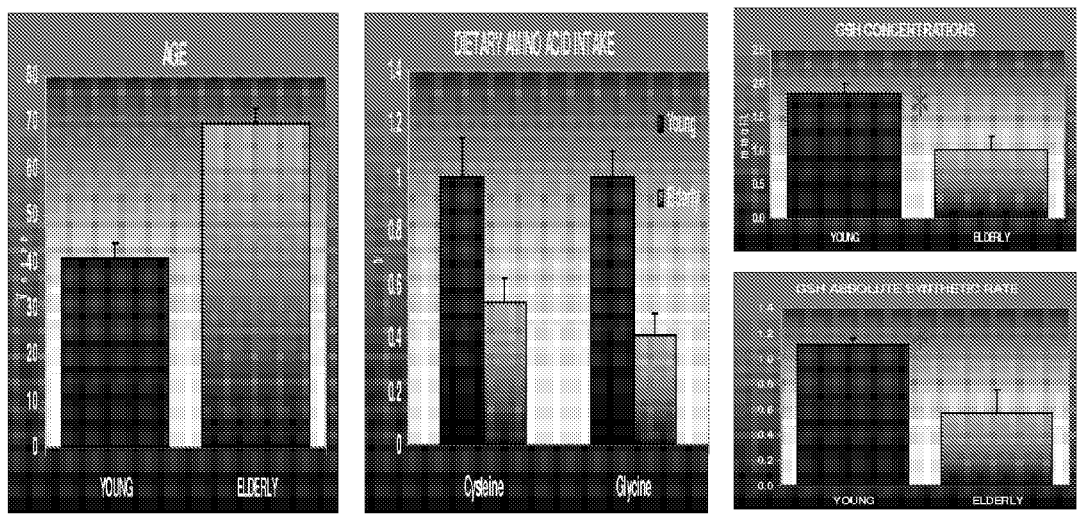
FIG. 8A shows basal GSH levels and precursor intake in young and elderly humans.
FIG. 8B shows GSH turnover in the elderly after precursor supplementation.
Figure 8:
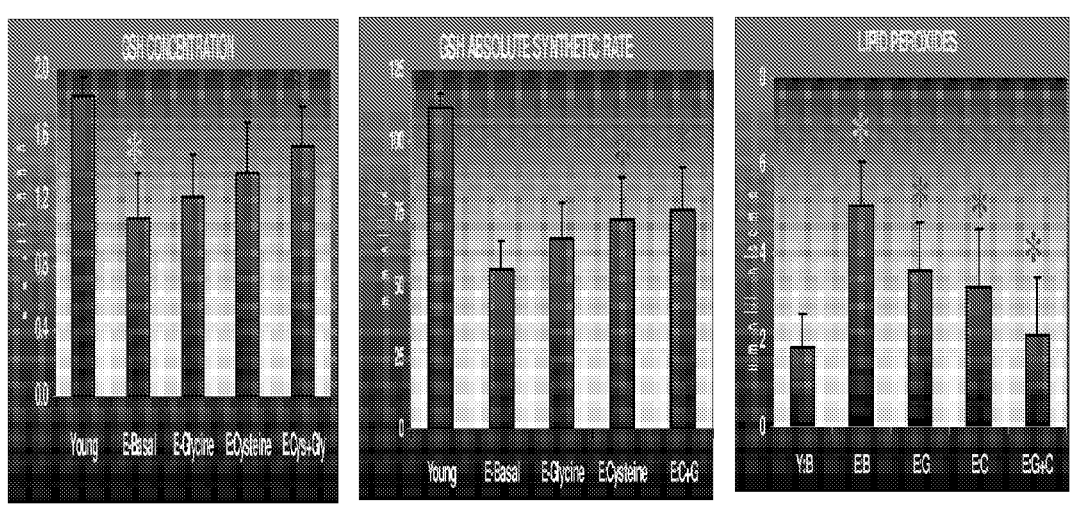

FIG. 8A shows basal GSH levels and precursor intake in young and elderly humans, and FIG. 8B shows GSH turnover in the elderly after precursor supplementation.

Figure 23:
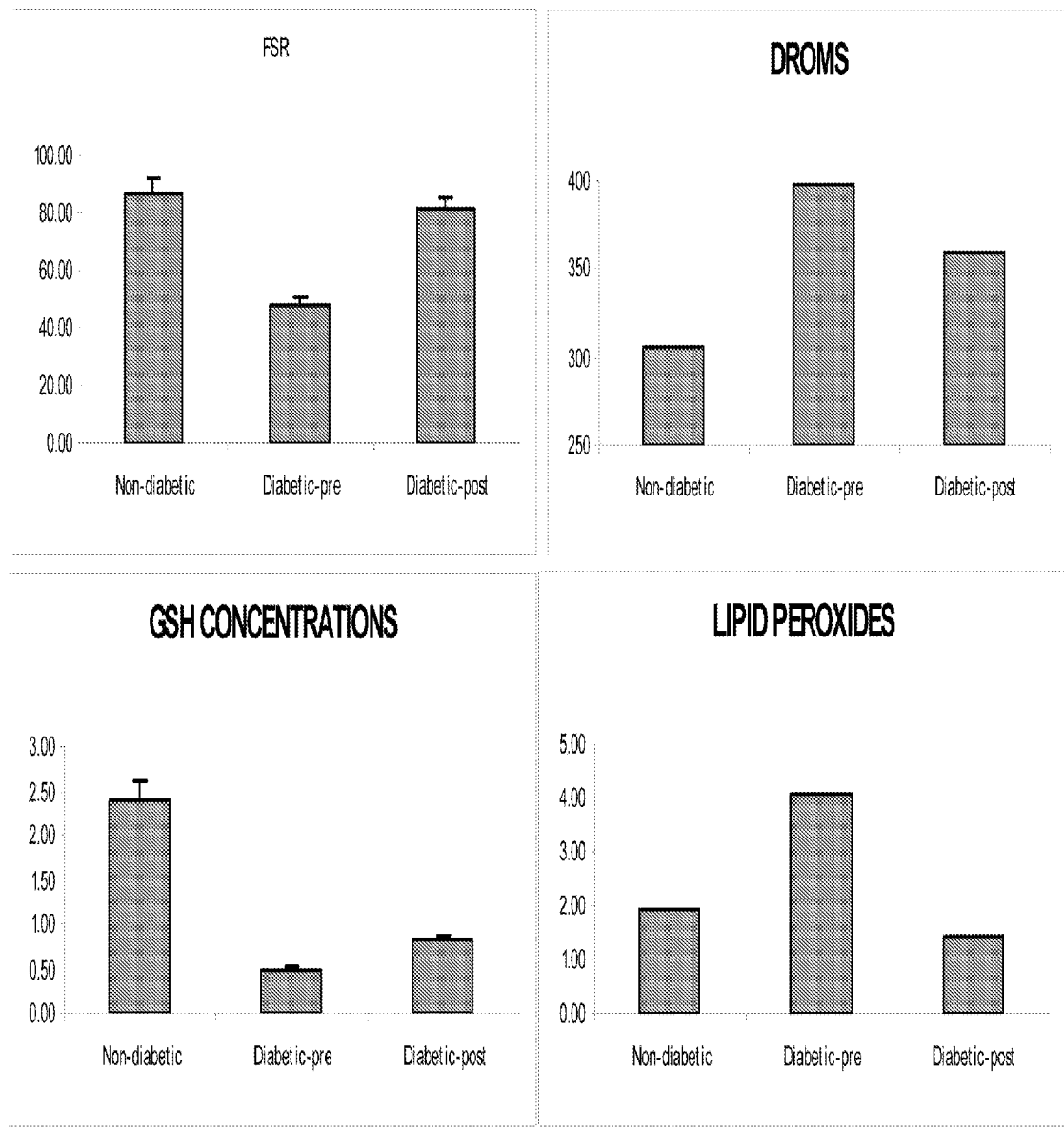
FIG. 23 shows that when precursors are provided in the diets, synthesis of glutathione increases significantly to that seen in non-diabetic humans, together with a significant fall in oxidative stress and markers of oxidative damage.

Similar to aging humans, humans with uncontrolled diabetes also have very low levels of glutathione, due to decreased synthesis—this leads to unopposed oxidative stress and elevated markers of damage. When precursors are provided in the diets, synthesis of glutathione increases significantly to that seen in non-diabetic humans, together with a significant fall in oxidative stress and markers of oxidative damage (see FIG. 23).

These data demonstrate, for the first time, that increased oxidative damage with aging in elderly humans is clearly linked to diminished GSH concentrations, and the underlying mechanism is decreased GSH precursor availability. Simple oral dietary supplementation with glycine and n-acetyl cysteine not only improves GSH synthetic rates and concentrations, but also results in normalizing plasma markers of tissue damage (lipid peroxides) to the levels of younger healthy controls. These results have a significant impact on the pathogenesis of oxidative damage with aging: simple dietary interventions with GSH precursors can restore GSH homeostasis and improve antioxidant status, and also have important preventive effects on the chronic complications of aging.

Thus, elderly patients are deficient in glutathione, resulting in elevated oxidative stress. GSH levels are low due to decreased synthesis, due to low precursor availability. Markers of damage due to oxidative stress are elevated in a state of GSH deficiency. Precursor supplementation improves GSH concentrations by elevating synthetic rates. The increase in GSH concentration reduces markers of damage due to oxidative stress.

Example 5

The Role of Glutathione on Fat Oxidation, Weight Regulation and Insulin Resistance with Aging The elevated risk of developing diabetes and cardiovascular disease with aging is associated with an increased incidence of insulin resistance and obesity, but underlying mechanisms are poorly understood. The inventor has found that compared to young healthy controls, aging is associated with diminished synthesis and low intracellular concentrations of glutathione (most abundant intracellular antioxidant) associated with increased oxidative stress and markers of oxidant damage; correcting glutathione deficiency by dietary precursor amino acid supplementation for 2 weeks results in a significant decrease in markers of oxidant damage. The mitochondrion is involved in both fatty acid oxidation and in the generation of superoxide free radicals in the electron transport chain, and maintaining adequate mitochondrial glutathione levels is critical in preventing oxidant injury. The inventor evaluated the effects of glutathione on fat oxidation, insulin resistance and body weight in healthy elderly humans and wild-type mice, in the basal glutathione depleted state, and after restoration of glutathione levels by simple oral dietary supplementation with glutathione precursor amino acids.

This translational study has two arms: (a) Human: 8 young controls and 8 non-diabetic elderly humans (60-75 years) were studied in the fasted state with measurements of glutathione concentrations, markers of oxidant damage, and respiratory gas exchange to compute fatty acid oxidation. (b) Animal: 8 young C57/B6 wild type mice (age 12-16 weeks), and two groups of 8 older (40-44 weeks) C57/B6 wild-type mice each were studied. The young mice and one group of 8 older mice were fed a regular chow diet (5% fat calories) for 4 weeks, and the second group of 8 older mice were fed an identical regular chow diet but with added supplements of glutathione precursors cysteine and glycine for 4 weeks. All animals had weekly weight measurements and were studied in the fasted state after the 4-week dietary intervention to measure respiratory gas exchange and energy expenditure by direct calorimetry; they also had measurements of food consumption, glucose and insulin tolerance, and hepatic glutathione concentrations.

The results were as follows: (a) Humans: Elderly humans had significantly lower red-cell glutathione concentrations compared to young controls (1.10±0.15 v 2.08±0.12 mmol GSH/L·RBC, p<0.05), associated with significantly higher levels of lipid peroxides and F2-isoprostanes. After a 16 h fast, elderly humans also had a significantly lower fat oxidation (9.91±0.76 v 5.86±0.58 umol/kg/min, p<0.0001), and elevated plasma concentrations of fatty acids (0.48±0.01 v 0.92±0.04 mEq/L, p<0.0001) and glucose (88±5 v 112±4 mg/dl, p<0.01). Glutathione precursor supplementation for 2 weeks in elderly humans resulted in a marked increase in the synthetic rate and red cell glutathione concentrations (1.10±0.15 v 2.07±0.31 mmol GSH/L·RBC, p=0.008), and falls in lipid peroxides (7.70±0.36 v 4.65±0.31 mmol/L·ROOH, p<0.01) and F2-isoprostanes (136±12 v 85±14 pg/ml, p<0.05). There were collateral benefits in fat and glucose metabolism with a striking increase in fat oxidation (5.86±0.58 v 8.55±0.22 umol/kg/min, p<0.001), and), and significant decreases in fasting plasma concentrations of fatty acids (0.92±0.04 v 0.59±0.07 mEq/L, p<0.05) and glucose (112±4 v 93±3 mg/dl, p<0.05). (b) Animal: Compared to young WT controls, older mice had lower hepatic glutathione concentrations (8.4±0.5 v 4.1±0.2 umol GSH/g liver, p<0.05), lower fat oxidation (77.1±1.0 v 58.3±2.1, p<0.0000) and had poor glucose tolerance. With 4 weeks of precursor supplementation, older mice had significant and striking increases in hepatic glutathione concentrations (4.1±0.4 v 5.7±0.3 umol GSH/g liver, p<0.05) and increased fat oxidation (58.3±2.1 v 64.5±1.4, p<0.01). Older mice receiving glutathione precursor supplementation lost 3.2% body weight (40.5±1.4 v 29.2±1.2 g, p<0.05) and improved insulin sensitivity, in contrast to the unsupplemented mice which gained 13% weight (38.2±1.8 v 43.1±1.8 g, p<0.001).

Figure 24:
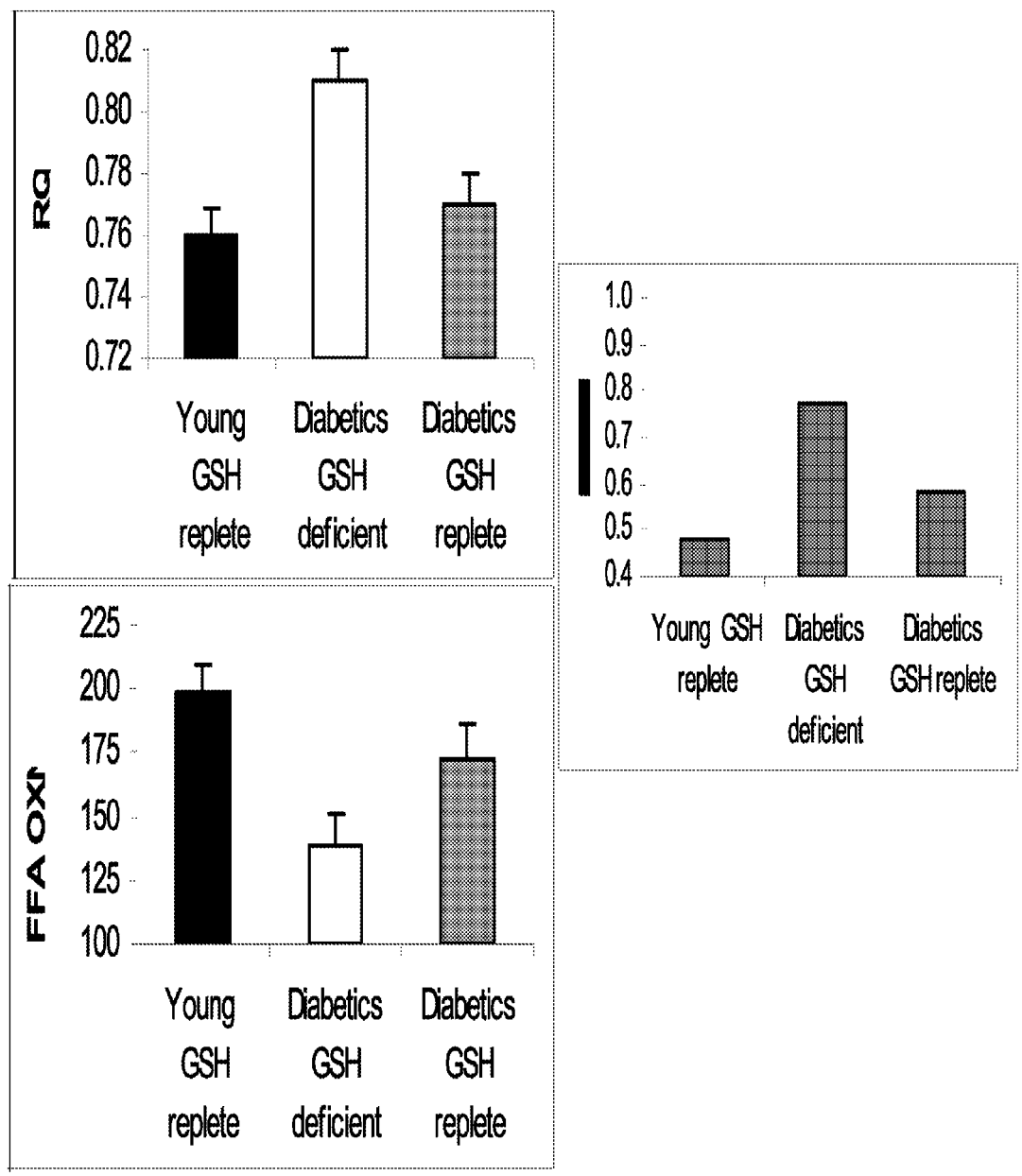
FIG. 24 shows that improving GSH also results in increasing fat oxidation and decreasing fatty acid concentrations in humans with uncontrolled diabetes.

FIG. 24 shows that improving GSH also results in increasing fat oxidation and decreasing Fatty acid concentrations in humans with uncontrolled diabetes.

These data indicate that there is a novel link connecting glutathione synthesis and concentrations to fat metabolism, weight regulation and insulin resistance. Glutathione deficiency in aging results in a diminished capacity to oxidize fat, leading to elevated fatty-acid and glucose levels, and insulin resistance. Stimulating glutathione synthesis with simple dietary amino acid precursors significantly improves tissue glutathione concentrations. Improving glutathione concentrations results in increased fat oxidation, and leads to reduced fasting plasma fatty-acid and glucose concentrations, decreased lipotoxic insulin resistance and decreased weight gain.

These observations indicate that glutathione deficiency occurs early in the process of aging, and the innovative use of a safe and inexpensive dietary supplement to correct defective fat-oxidation and reduce fatty-acid concentrations is a useful antioxidant therapy as a novel nutritional approach to combat at least insulin resistance, obesity and diabetes in aging.

Figure 11:
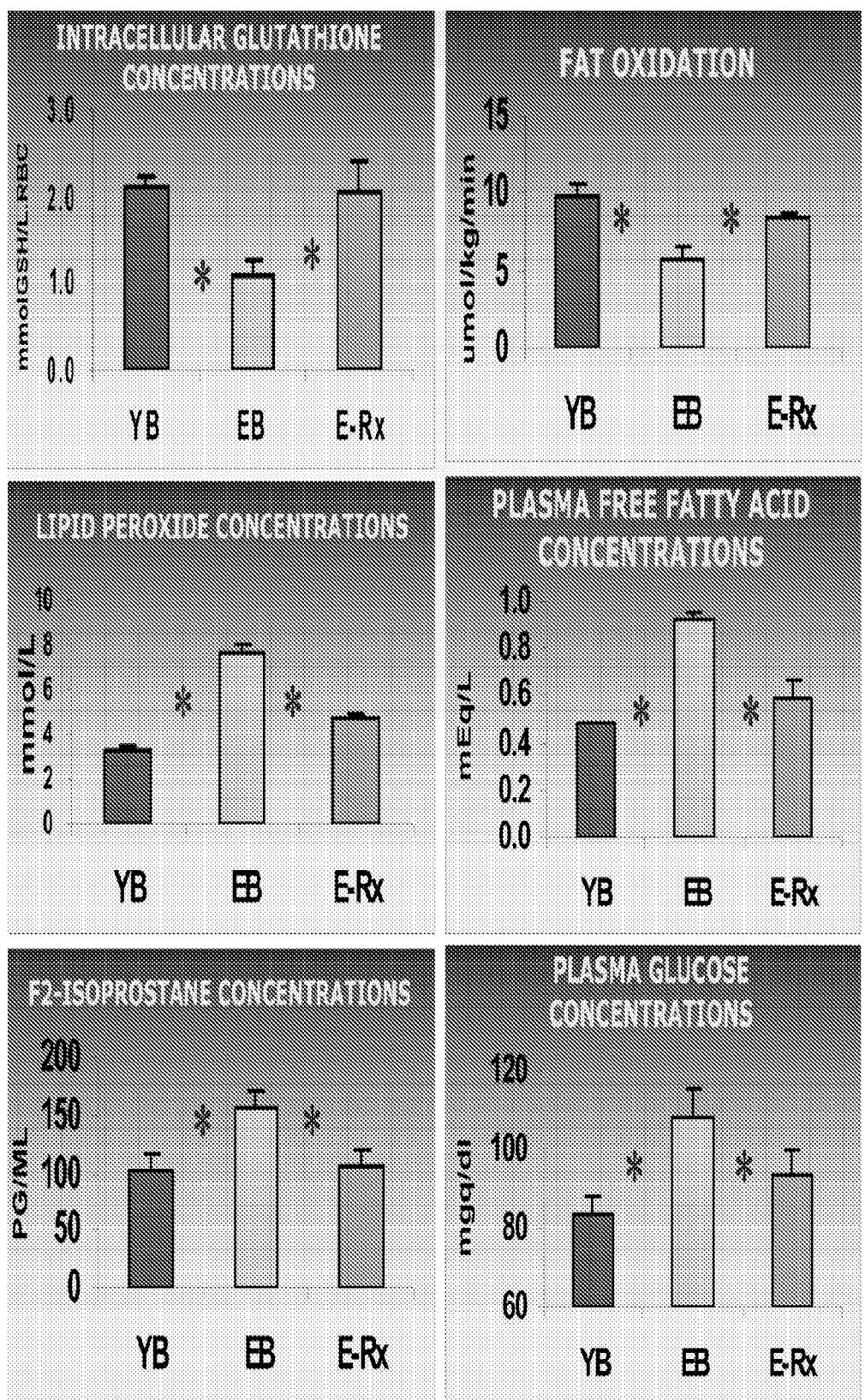
FIG. 11 demonstrates human studies related to the role of GSH on fat oxidation, weight regulation, and insulin resistance.
Figure 12:
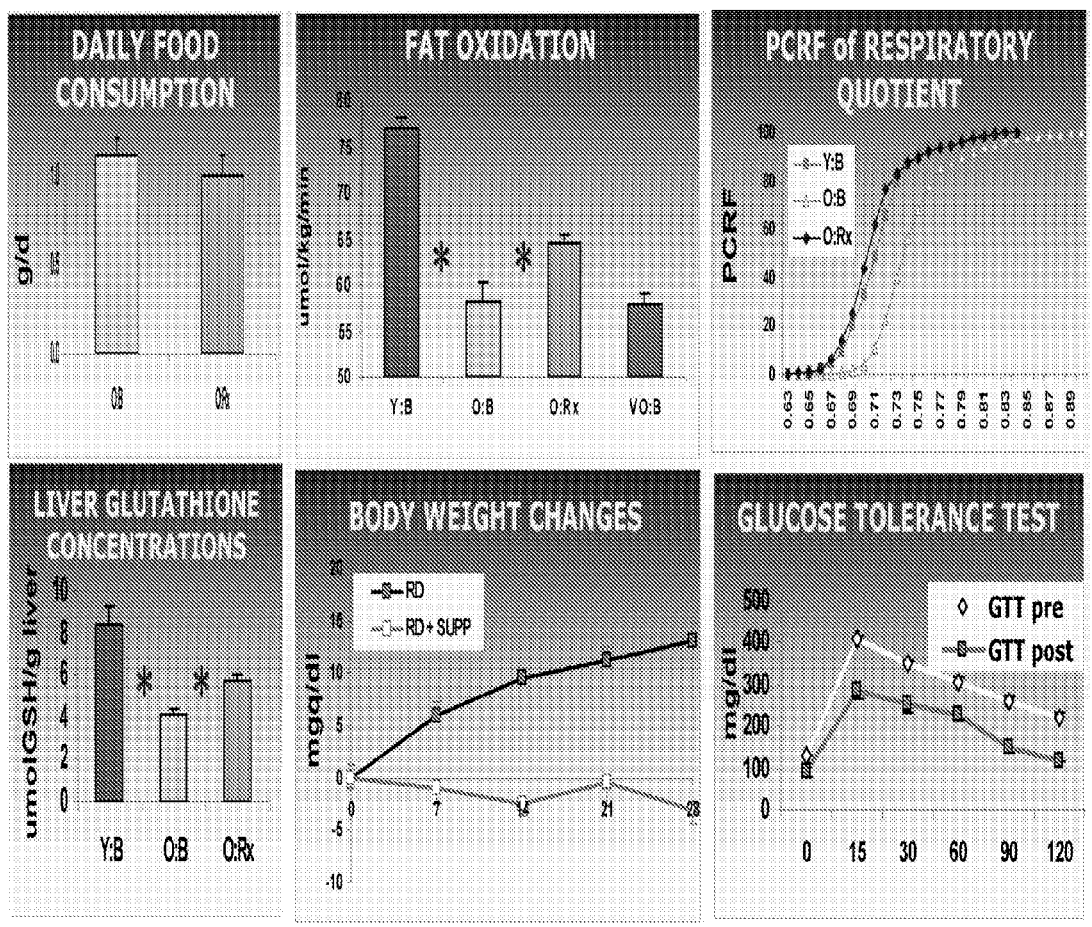
FIG. 12 demonstrates animal studies related to the role of GSH on fat oxidation, weight regulation, and insulin resistance.
Figure 13:
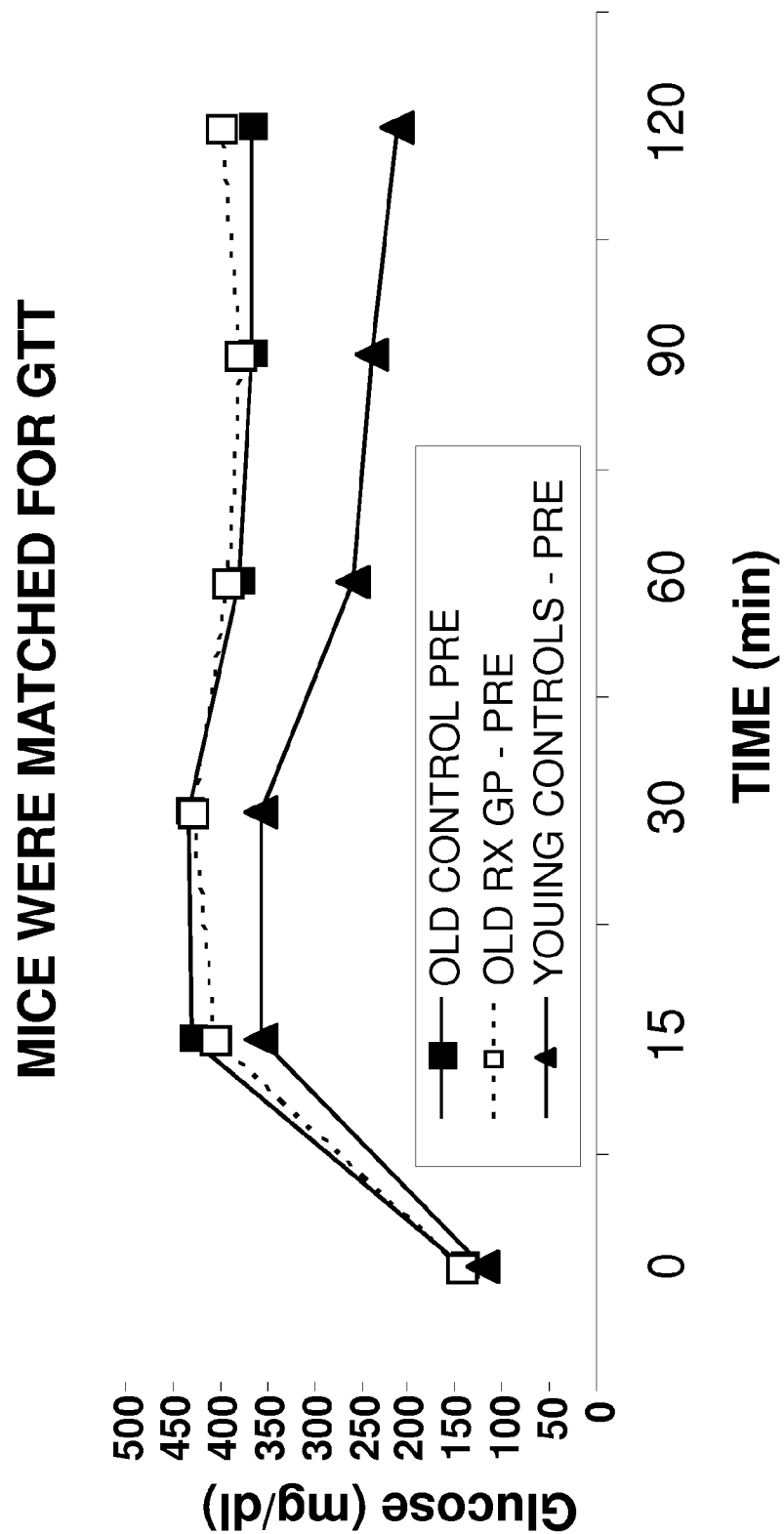
FIG. 13 shows that mice were matched for GTT levels between the old control PRE and Old RX GP-PRE in an exemplary study for aging associated with GSH deficiency.
Figure 14:
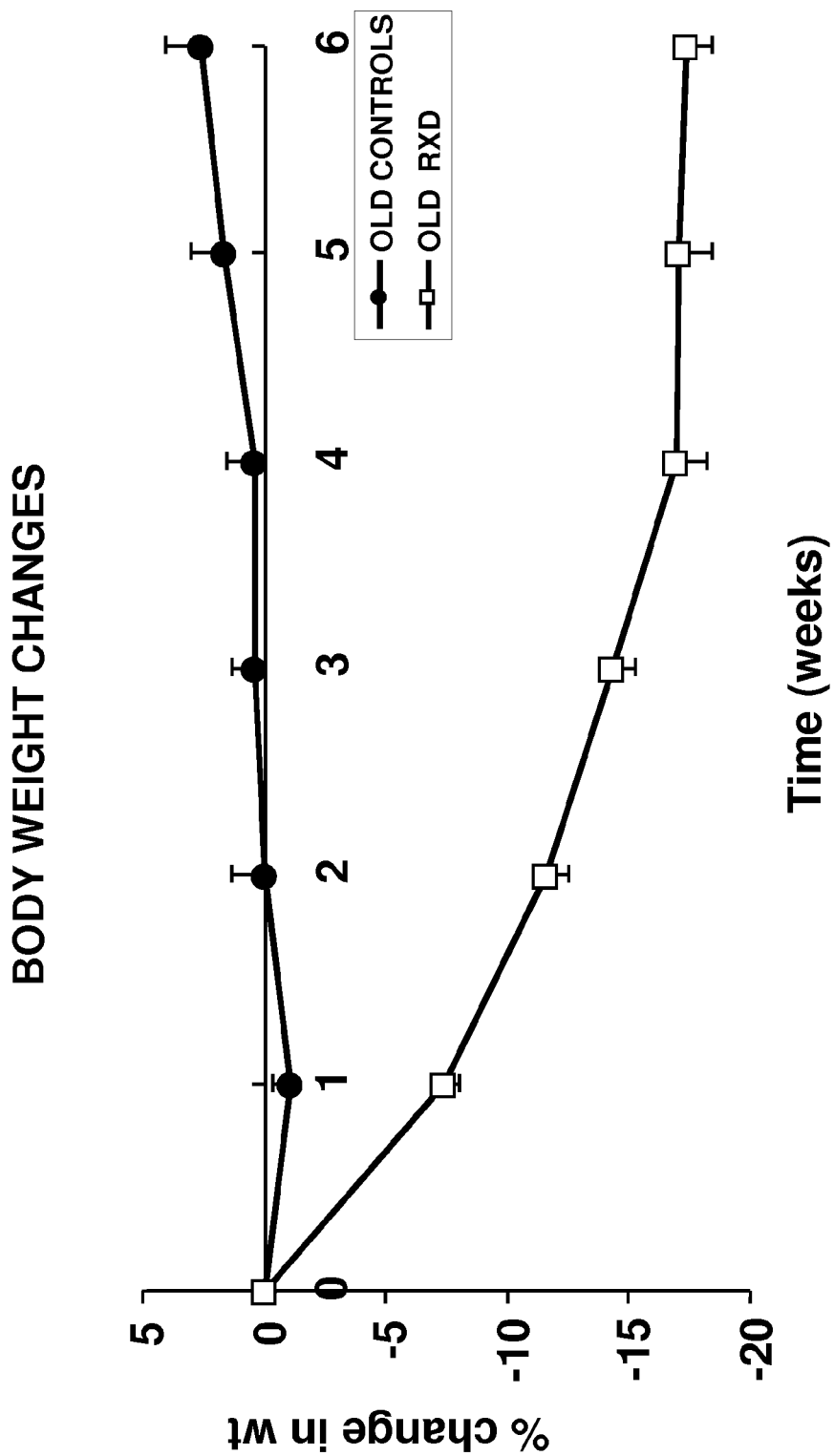
FIG. 14 demonstrates body weight changes in an exemplary study for aging associated with GSH deficiency.
Figure 15:
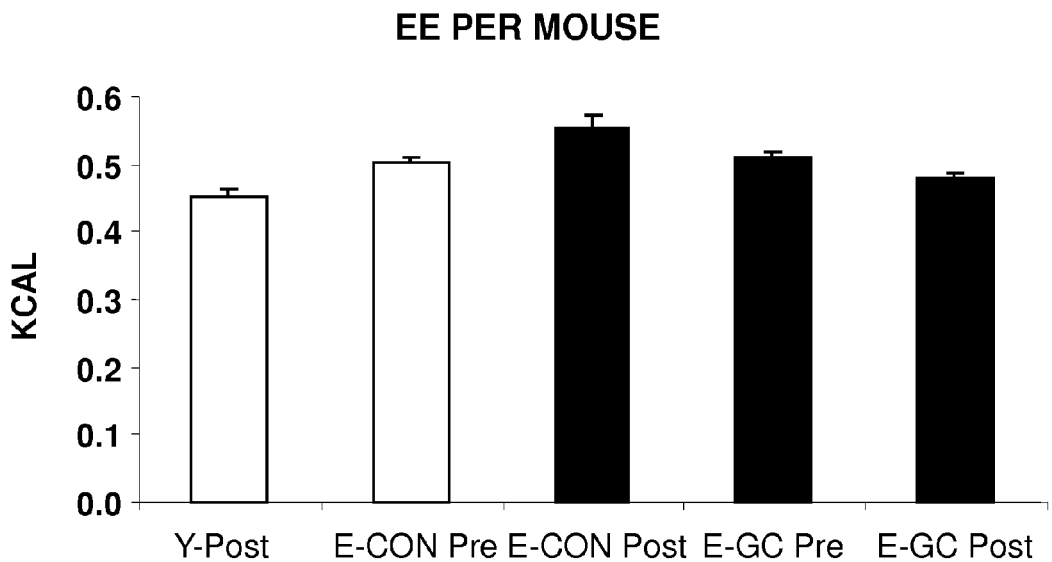
FIG. 15 shows EE per mouse and per KG LBM in an exemplary study for aging associated with GSH deficiency.
Figure 15:
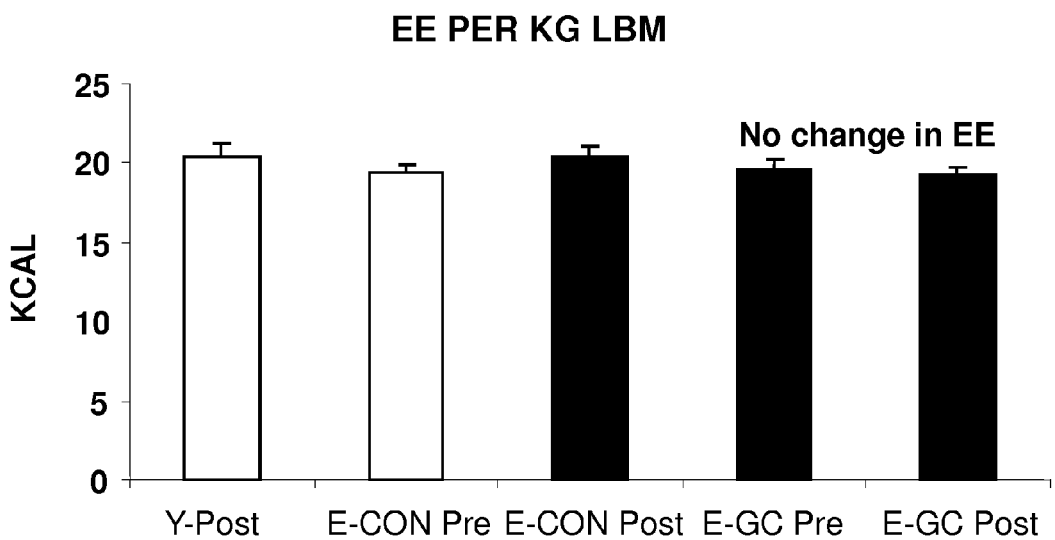
Figure 16:
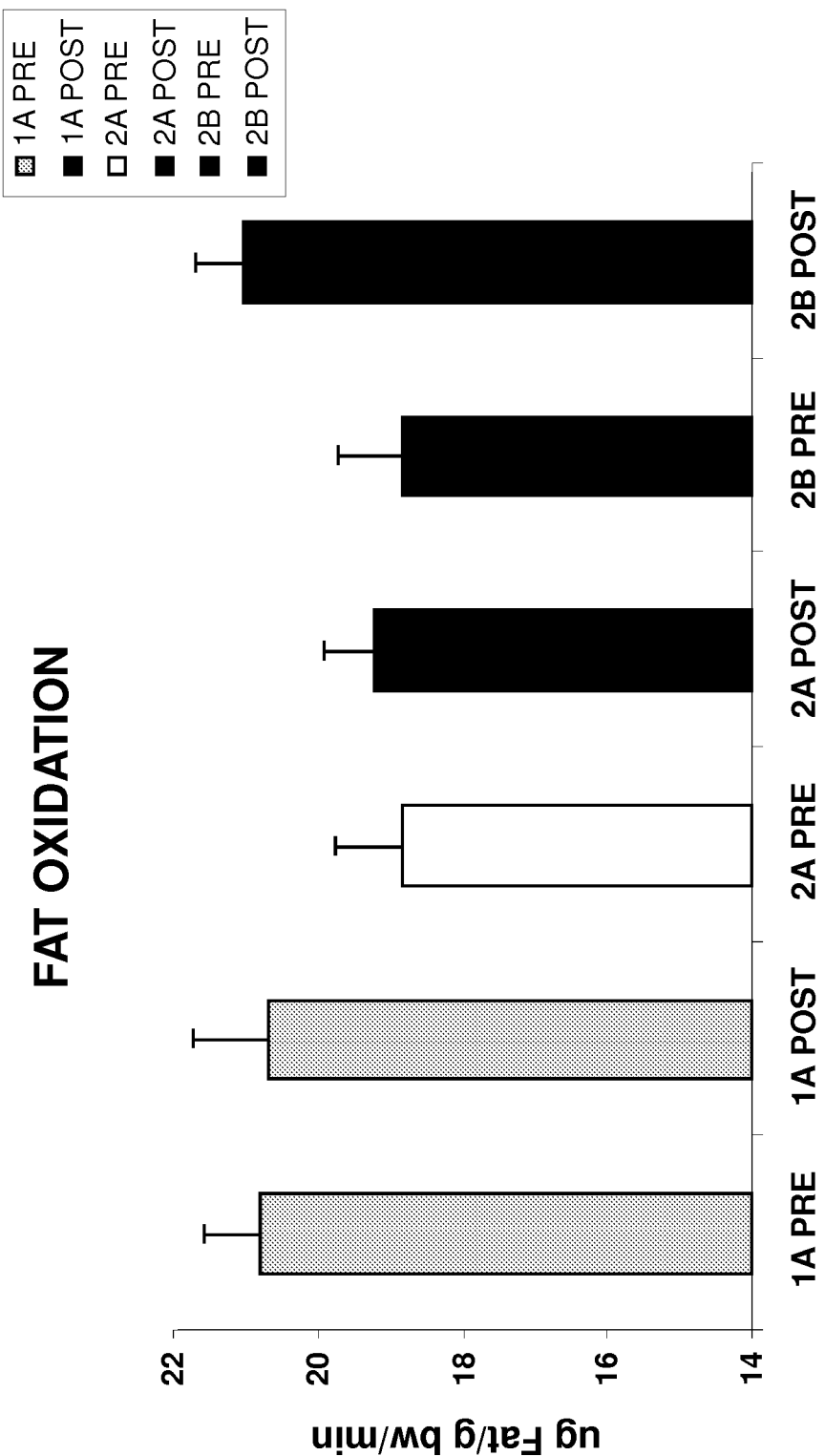
FIG. 16 demonstrates fat oxidation in an exemplary study for aging associated with GSH deficiency.
Figure 17:
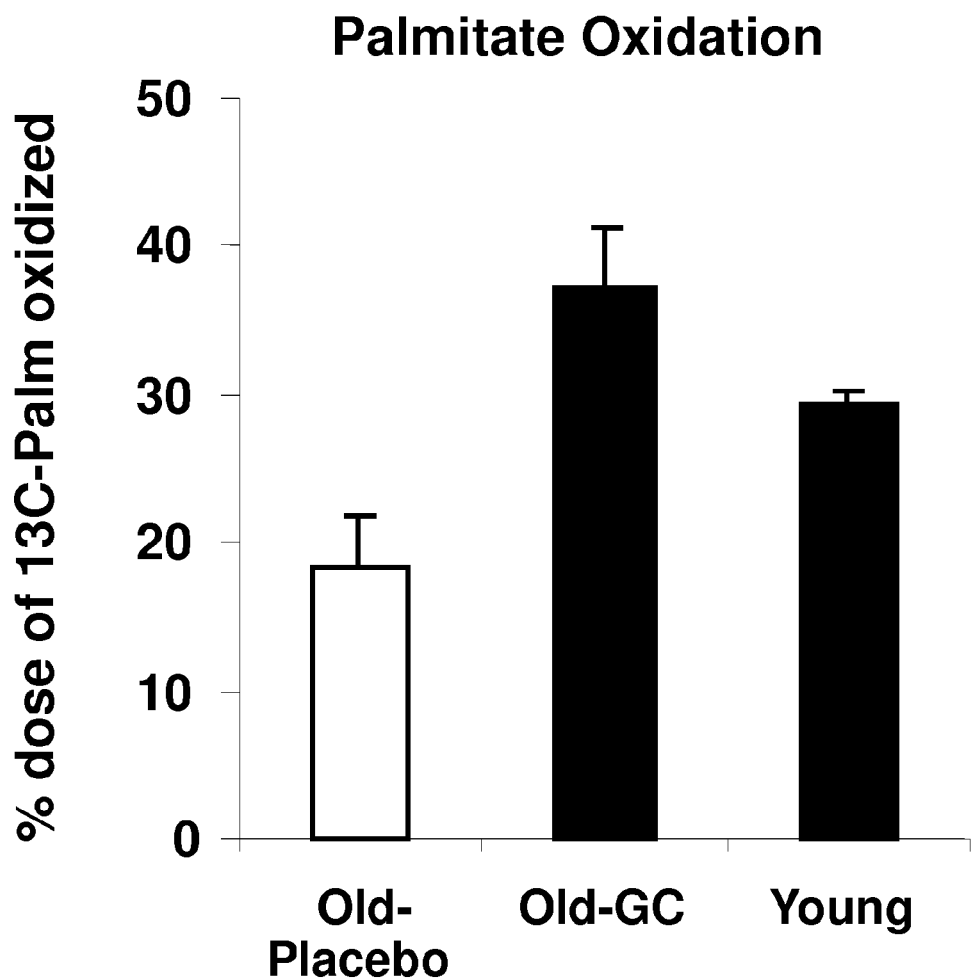
FIG. 17 shows $^{13}C_1$ palmitate oxidation in an exemplary study for aging associated with GSH deficiency, wherein treated old mice have a significantly higher oxidation of fat than untreated old mice, and even exceed that of young mice.
Figure 18:
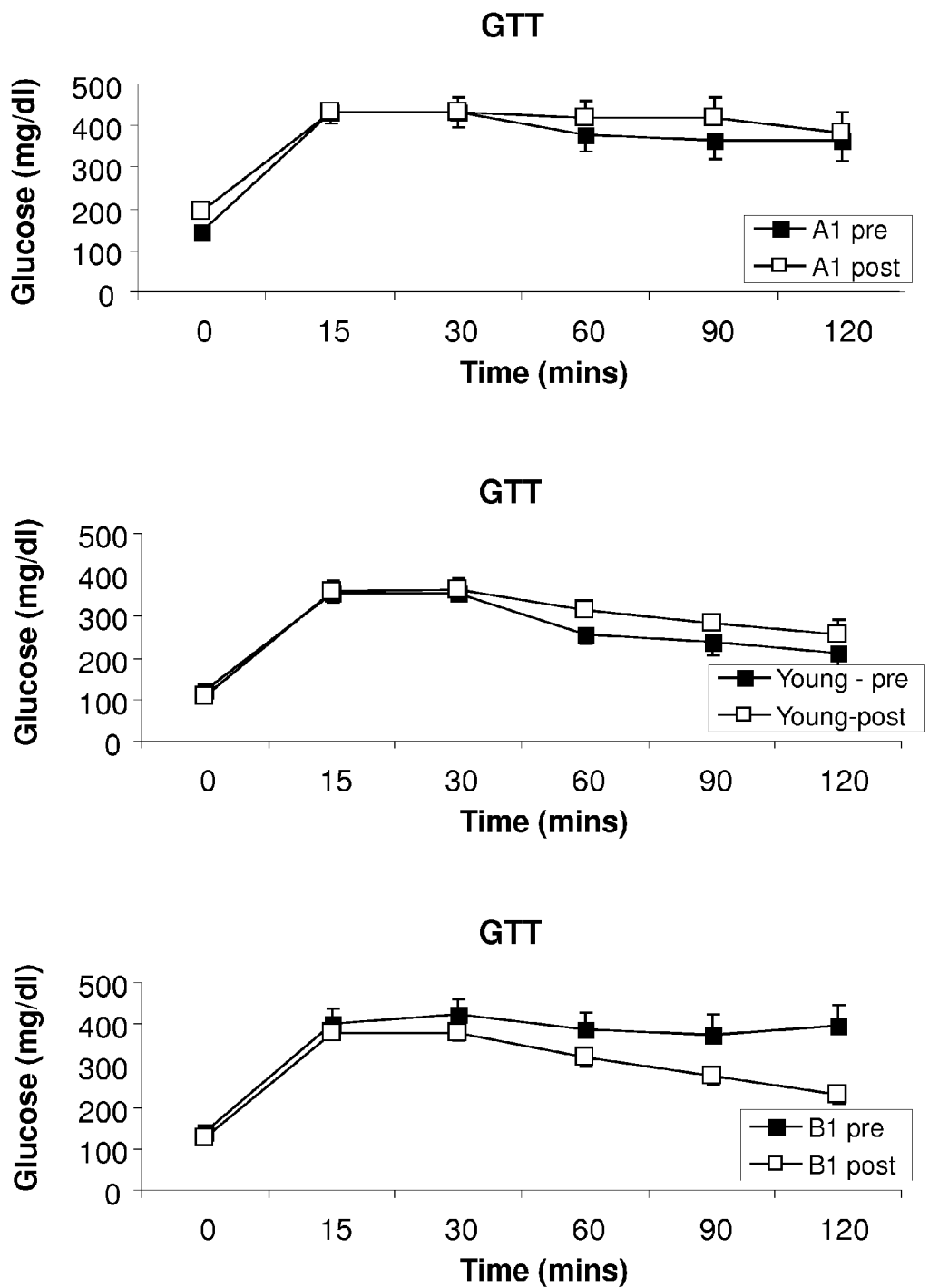
FIG. 18 demonstrates GTT in an exemplary study for aging associated with GSH deficiency.
Figure 19:
FIG. 19 shows data from an exemplary study for aging associated with GSH deficiency, in particular glucose tolerance after 6 weeks. Treated old mice have a significantly improved glucose tolerance (insulin resistance) compared to untreated old mice, and are similar now to young mice.
Figure 20:
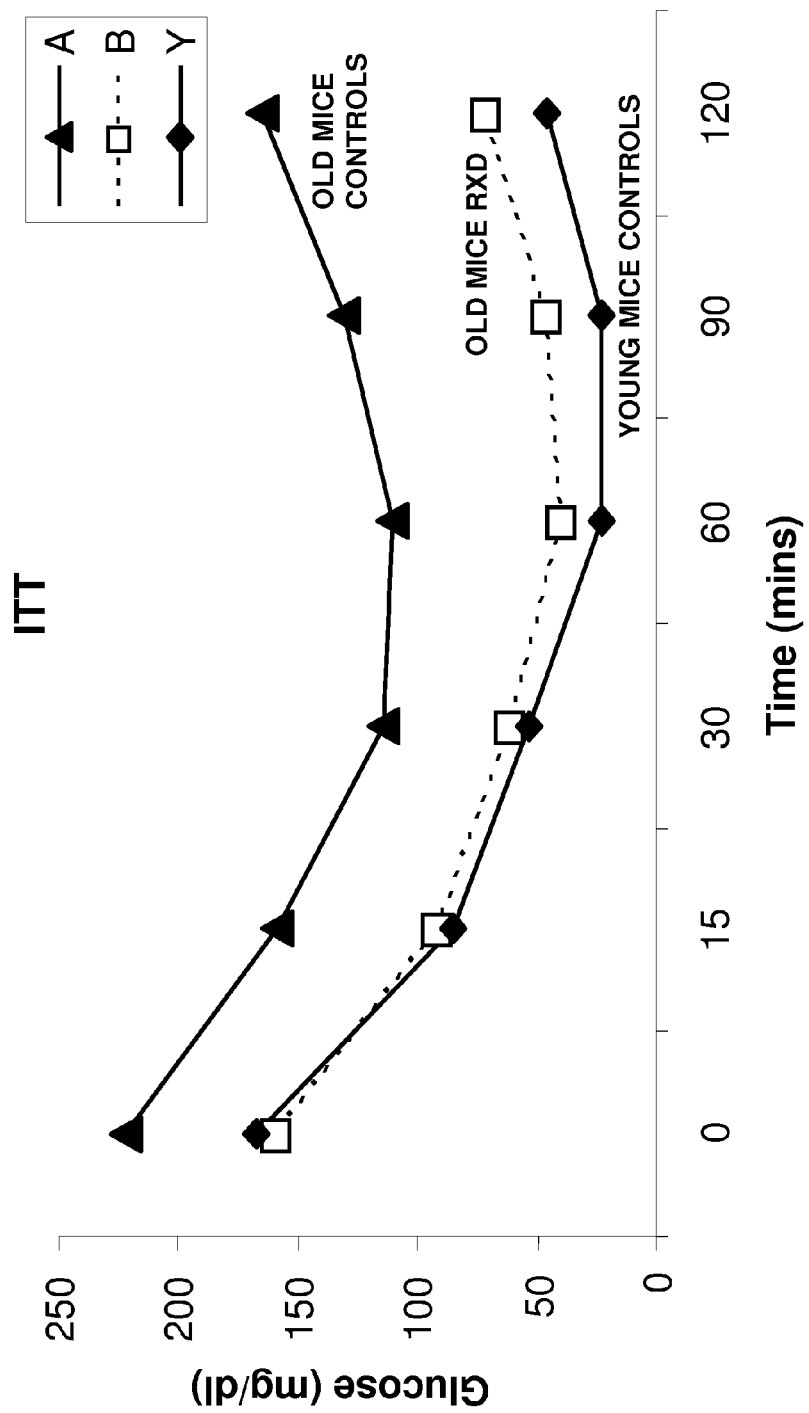
FIG. 20 demonstrates ITT in an exemplary study for aging associated with GSH deficiency; in particular, insulin sensitivity after 6 weeks is demonstrated. This graph shows that treated old mice have a significantly improved insulin sensitivity compared to untreated old mice and are similar now to young mice.
Figure 21:
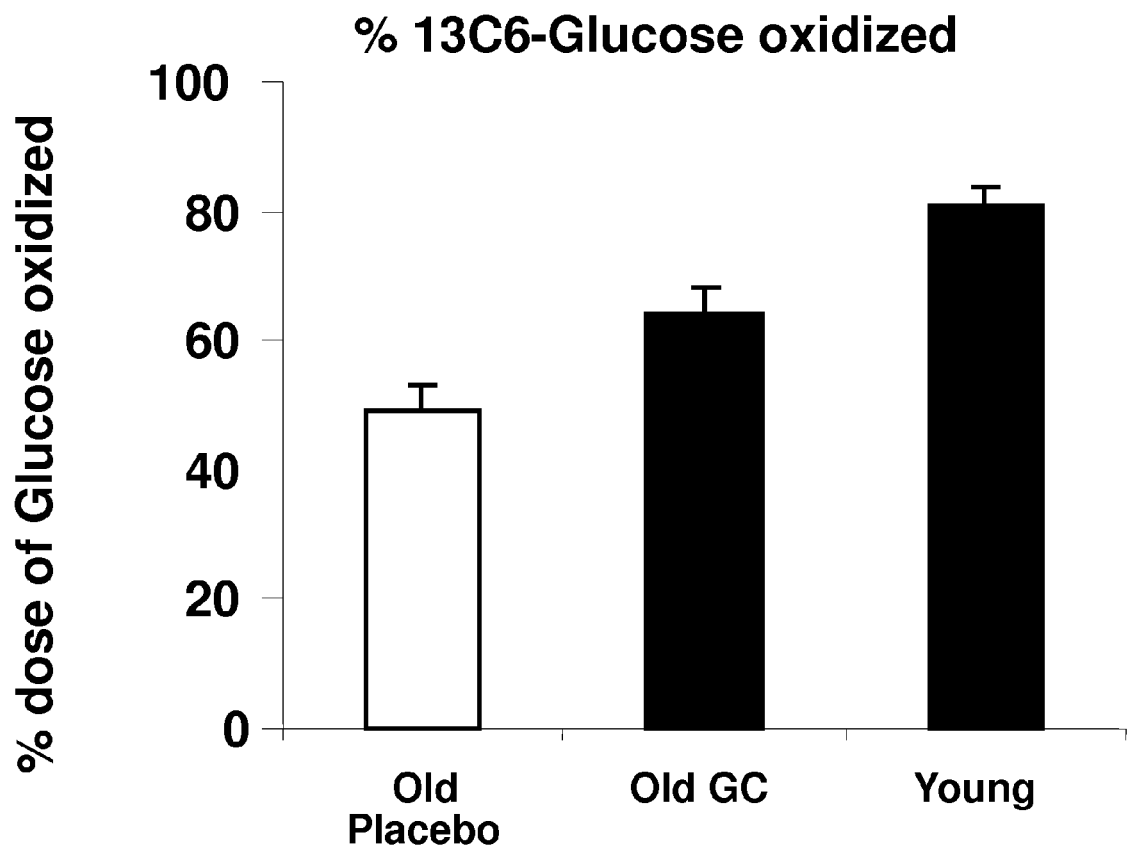
FIG. 21 demonstrates % $^{13}C6$-glucose oxidized in an exemplary study for aging associated with GSH deficiency.
Figure 22:
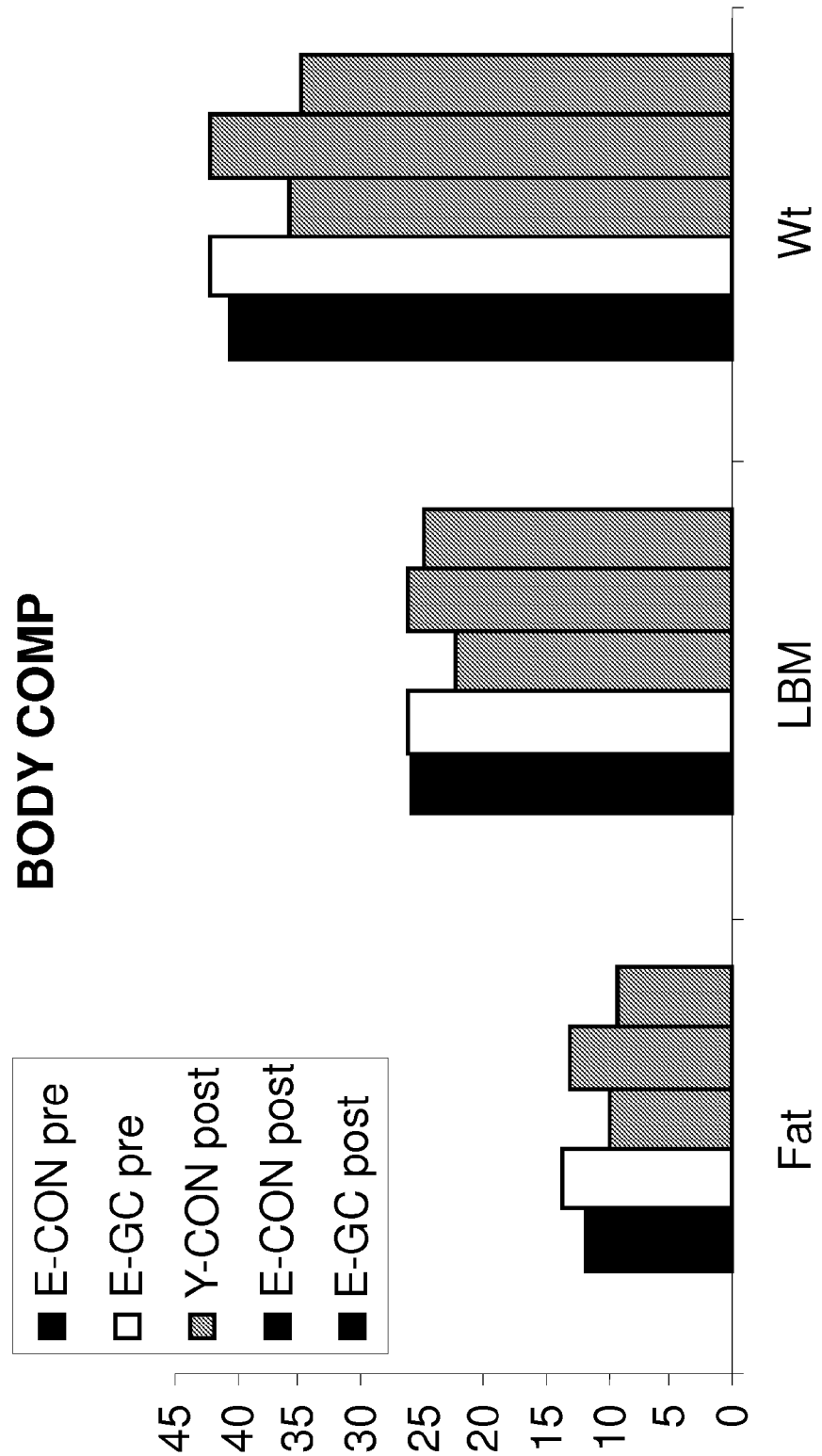
FIG. 22 shows body composition in an exemplary study for aging associated with GSH deficiency.

FIG. 9 illustrates exemplary study design for humans and animals. FIG. 10 demonstrates exemplary measurements related to human studies for characterizing glutathione role on fat oxidation, weight regulation and insulin resistance with aging. FIG. 11 provides the human studies referred to above in this example, and FIG. 12 provides the animal studies referred to above in this example.

Example 6

Aging is Associated with GSH Deficiency

In certain aspects, aging is associated with Glutathione (GSH) deficiency. This leads to deficient capacity to oxidize fat, in turn leading to obesity, being overweight, and insulin resistance.

In a human study, the inventor has shown that feeding GSH precursor proteins in the diet improves GSH levels. The elderly humans had much lower capacity to oxidize fat compared to young humans. After only 14 days of consuming the GSH precursor proteins the elderly humans not only normalized GSH production and concentrations, but they also restored their capacity to oxidize fat to that of young controls. This resulted in a 36% drop in their fatty acid levels.

Taking the concept to a mouse model, 3 groups of male mice were studied: young controls (14 weeks), and 2 groups of old controls (70 weeks). The old mice were matched for age, weight and glucose tolerance. Both groups of old mice received identical amounts of food, and the composition of the food was identical in terms of carbohydrate, fat and protein, except that the treated group's protein was enriched with GSH precursors, and the control group's protein did not have GSH precursors.

After 6 weeks of supplementation, the Rxd group decreased body weight by 15%, which was entirely fat weight (no change in lean mass), increased fatty acid oxidation, improved their glucose tolerance and insulin sensitivity together with a significant increase in liver and muscle GSH.

These data (provided in FIGS. 13-22) indicate that there GSH manipulation results in significant metabolic benefits in terms of insulin resistance, dyslipidemia and body weight in mice due to increase fat oxidation. Early data from humans indicate that GSH manipulation results in increased fat oxidation and improves dyslipidemia, and could have similar favorable benefits on insulin resistance and body weight. In specific embodiments, there is fat oxidation of $^{13}C_1$ palmitate, wherein the oxidation of a labeled fat as a direct measurement of fat oxidation, wherein old mice have a significantly lower oxidation of fat than young mice.

Example 7

GSH and Neurodegenerative Disease in Aging

Figure 25A:
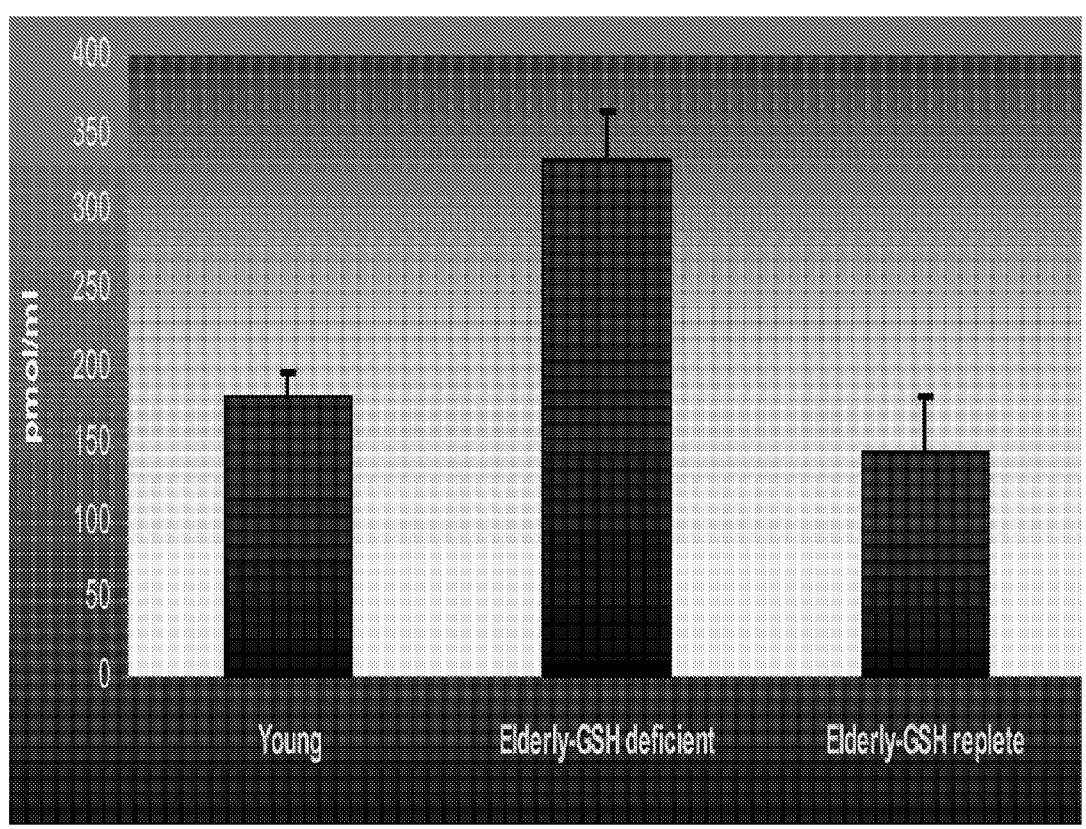
FIG. 25 demonstrates that improving GSH also results in decreasing F3 isoprostanes (FIG. 25A) and decreasing F2 isoprostanes (FIG. 25B) in elderly humans.

Improving GSH also results in decreasing F3 isoprostanes in elderly humans. Since F3 isoprostanes are markers of oxidative stress mediated damage in the brain, this has important implications for neurodegenerative disease in aging (FIG. 25A). F2-isoprostanes are biomarkers of ongoing damage due to oxidative stress.

Example 8

F2 Isoprostane Levels and GSH in Elderly Humans

Figure 25B:
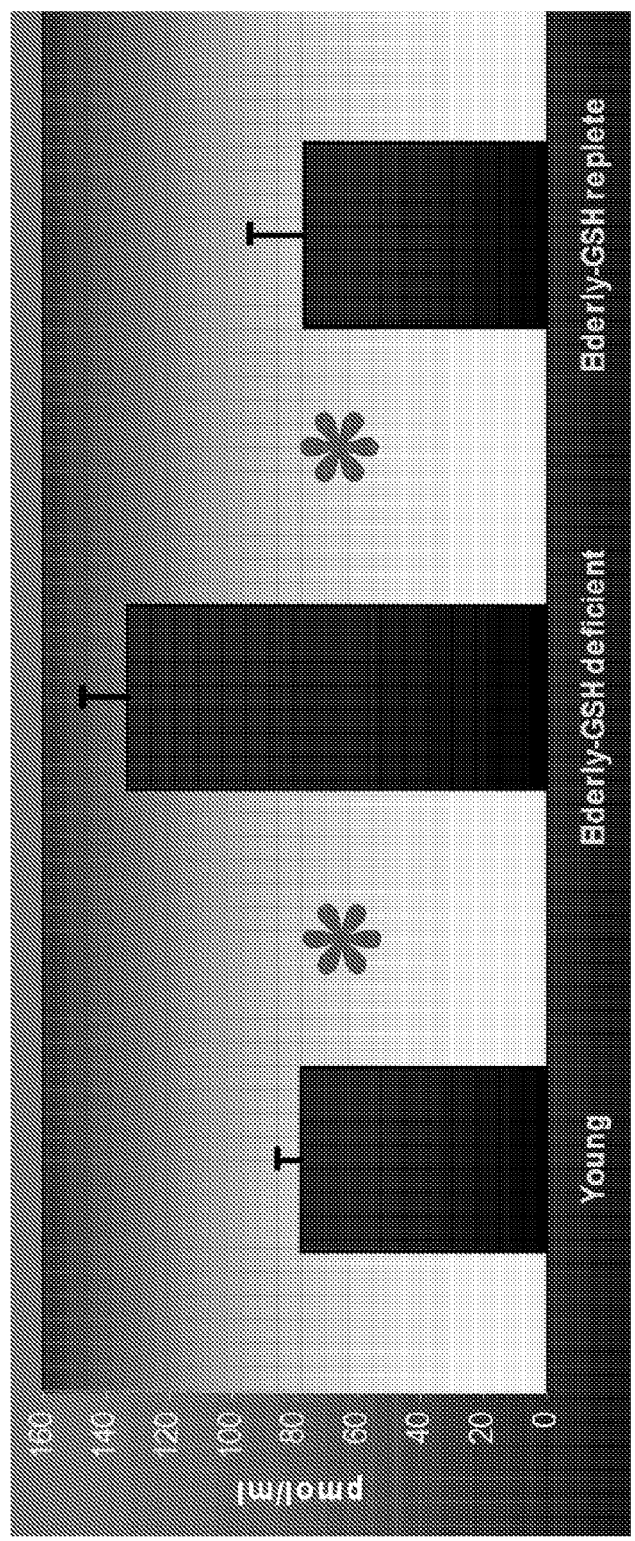

Compared to young humans, elderly humans have increased F2 isoprostanes in the glutathione deficient state, indicating that there is increased damage due to oxidative stress (FIG. 25B). When glutathione synthesis and concentrations are corrected with dietary supplementation of cysteine (as N-acetylcysteine) and glycine, the F2 isoprostane levels in elderly humans fall to that seen in younger humans, indicating that there is no further damage as a result of the protective actions of glutathione.

Example 9

Role of Glutathione on Obesity, Insulin Resistance and Dyslipidemia in Aging In the present example and previous examples herein, the role of glutathione on obesity, insulin resistance, and dyslipidemia in aging was examined. Outcome measures include whole-body fatty acid oxidation, total body weight, fat and lean mass, glutathione concentrations in liver and muscle, energy expenditure, insulin resistance (from glucose tolerance tests), insulin simulated glucose disposal, total cholesterol and triglycride concentrations, and the exemplary molecular markers P-AMPK/AMPK, P-ACC/ACC, AND PGC1α.

Figure 27:
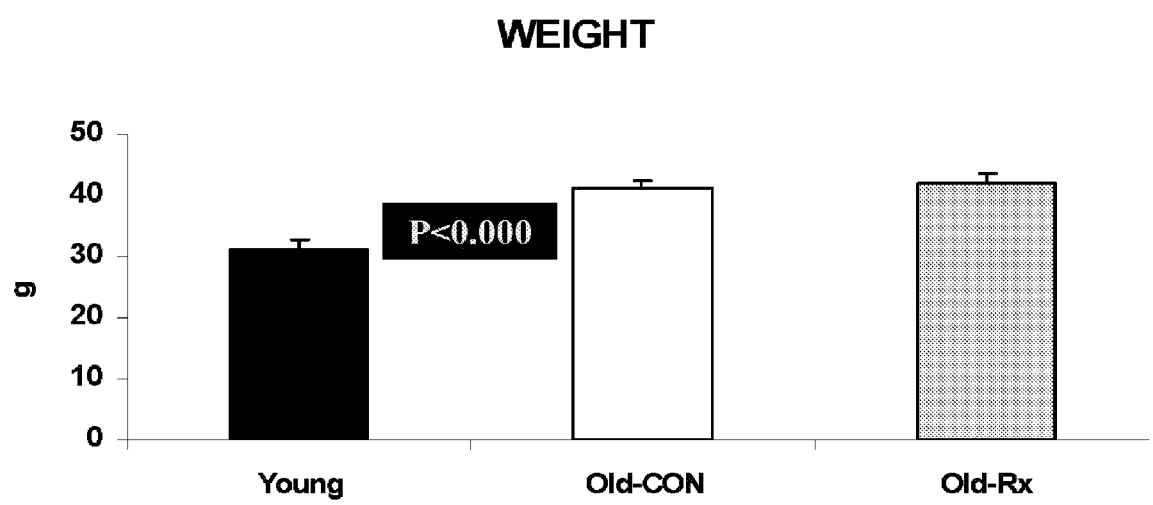
FIG. 27 shows basal body weights in certain groups of mice.

FIG. 27 shows a study utilizing one group of young mice and two groups of old mice. Of these old mice, one group is control (CON) and the other group receives the cysteine and glycine precursors. The graph shows that old mice weigh significantly more than young mice, and that both groups of old mice are identical in body weight. In particular cases, these mice are employed in further studies described herein. Old mice do weigh more than young mice, and MRI data show that they have a higher fat content. The 2 groups of old mice were so randomized to be equal in weight so that the study could be done.

Figure 28:
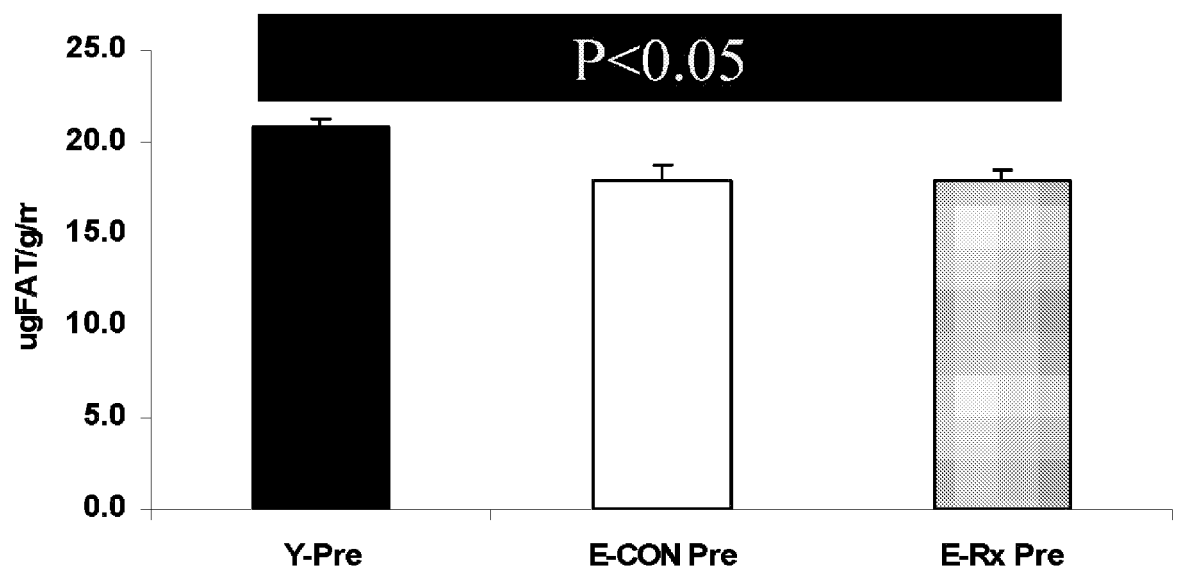
FIG. 28 shows basal whole-body fat oxidation in young mice, control old mice, and experimental old mice that have not received treatment.

FIG. 28 shows basal whole-body fat oxidation in young mice, control old mice, and experimental old mice that have not received treatment. Fat oxidation in old mice is significantly worse than young mice, and both groups of old mice are identical in terms of whole-body fat oxidation.

Figure 29:
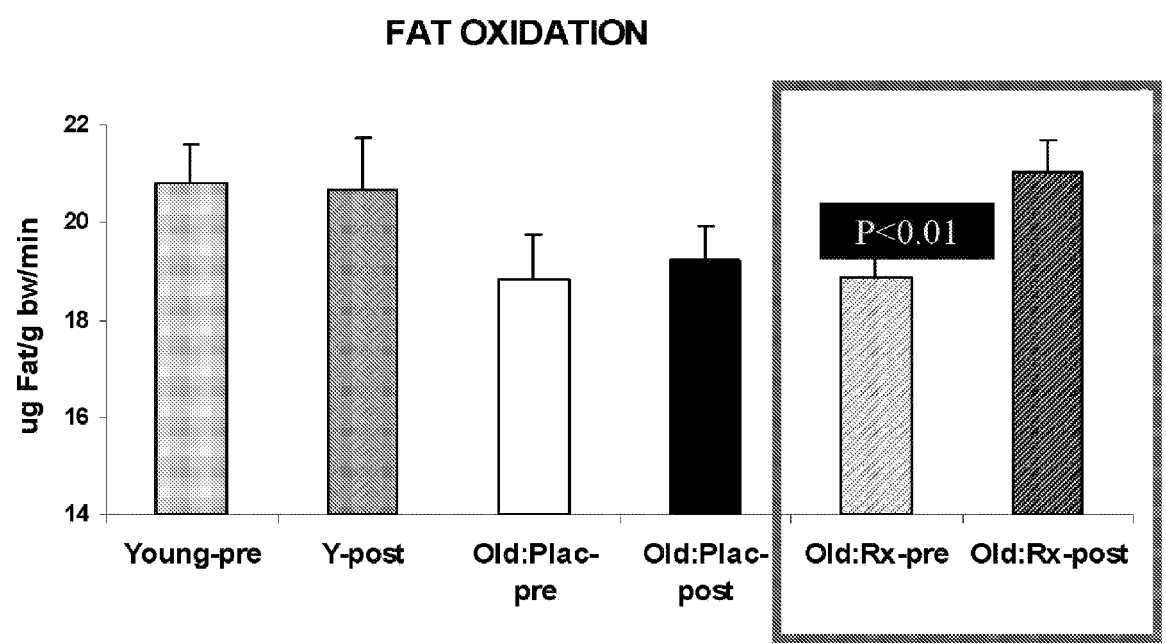
FIG. 29 illustrates fat oxidation by calorimetry of young mice versus untreated old mice and treated old mice.

FIG. 29 shows fat oxidation by calorimetry. After six weeks, there are no significant changes in fat oxidation of young mice (see two bars on the left). After six weeks, there are no significant changes in the fat oxidation of old mice, and this remains much lower than that seen in the young mice (see middle two bars). After six weeks of treatment with cysteine and glycine, there is a significant increase in the fat oxidation of treated old mice, and this reaches levels that are seen in the young mice.

Figure 30:
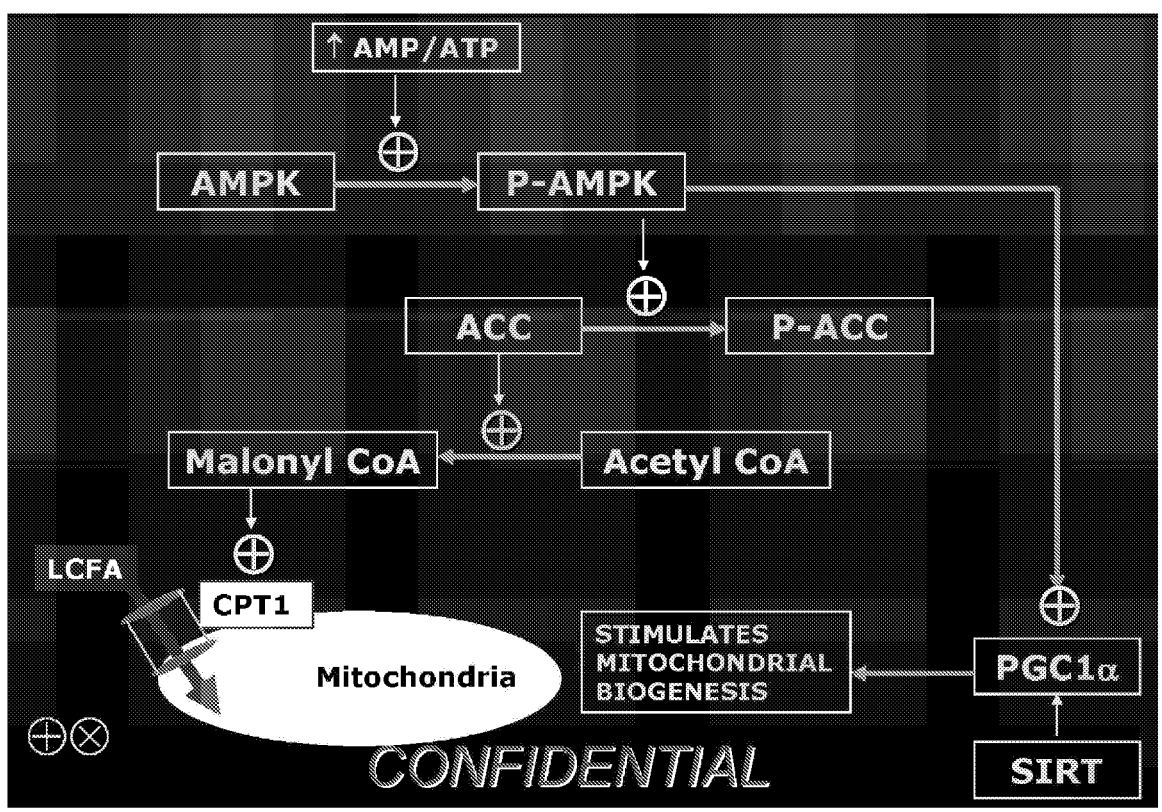
FIG. 30 illustrates the AMPK signaling cascade.
Figure 31:
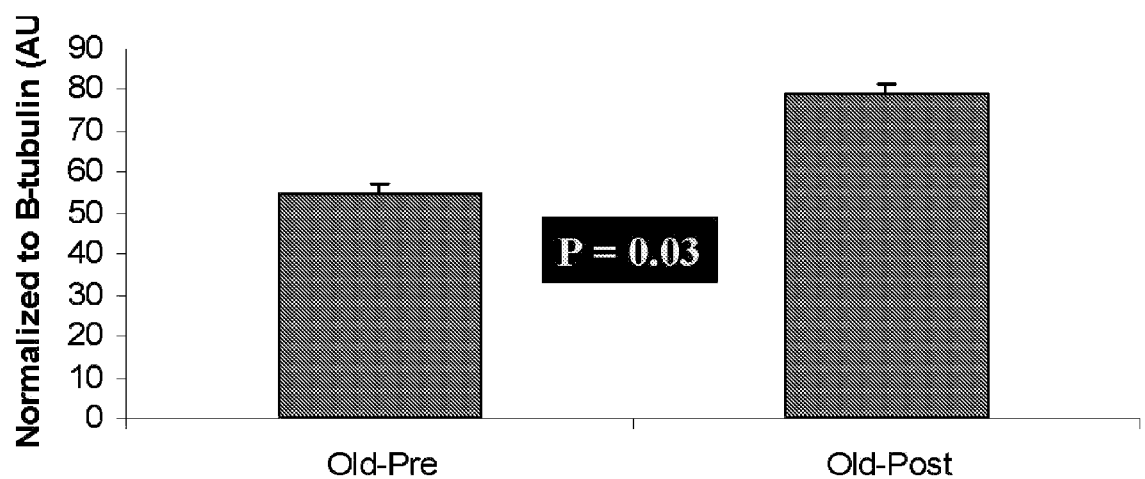
FIG. 31 illustrates phosphorylated AMPK to AMPK ratio in the liver.
Figure 32:
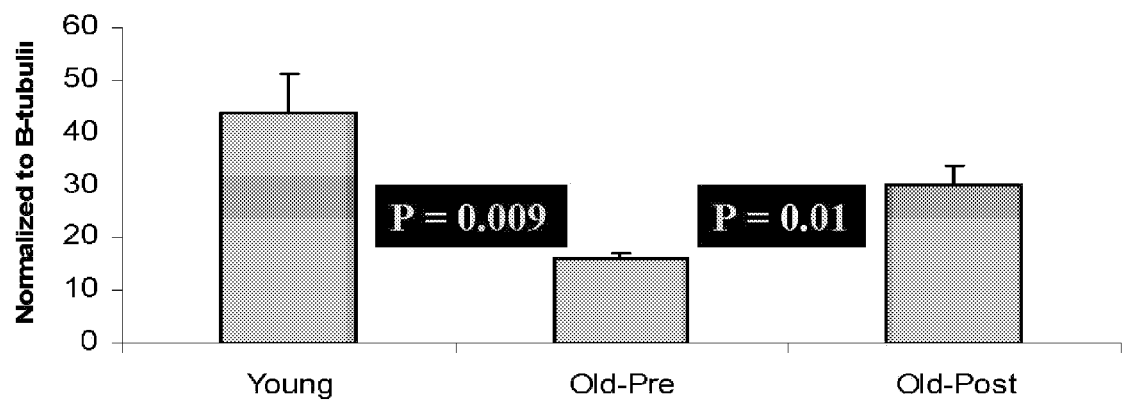
FIG. 32 shows the ratio of phosphorylated ACC to ACC in the liver.
Figure 33:
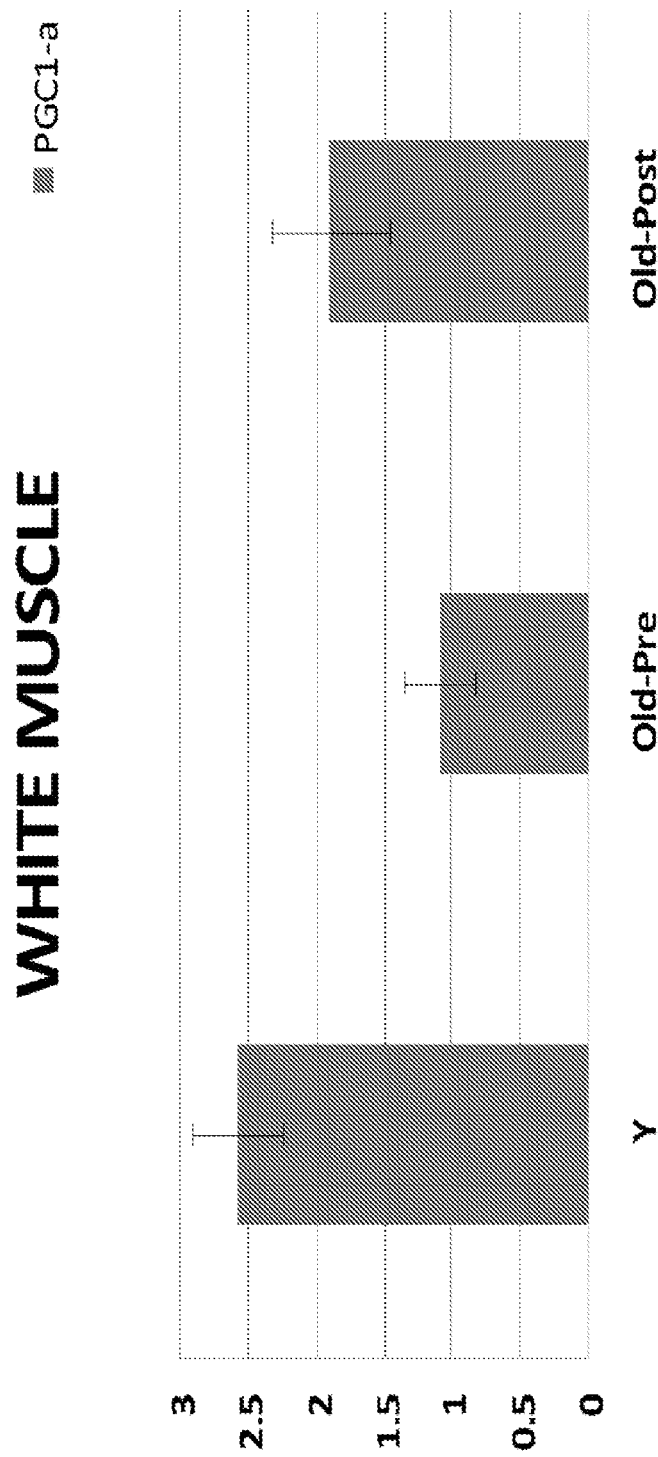
FIG. 33 shows energy metabolism in white muscle via PGC1-a levels in the tested mice.

FIG. 30 illustrates the AMPK signaling cascade. FIG. 31 shows the AMPK cascade in the context of the invention. Phosphorylation of AMPK (i.e. an increased ratio of P-AMPK to AMPK) ultimately increases entry of LCFA into the mitochondria. In FIG. 31, this occurs more in treated old mice than in untreated old mice. In FIG. 32, phosphorylation of ACC (i.e. an increased ratio of P-ACC to ACC) ultimately decreases entry of LCFA into the mitochondria, and the graph shows that treated old mice show this more than untreated old mice. In FIG. 33, untreated old mice (unsupplemented) have lower PGC1a than young mice. After 6 weeks of glycine+cysteine supplementation in the treated old mice, the PGC1a increases, indicating that there are beneficial effects on mitochondrial biogenesis.

Figure 34:
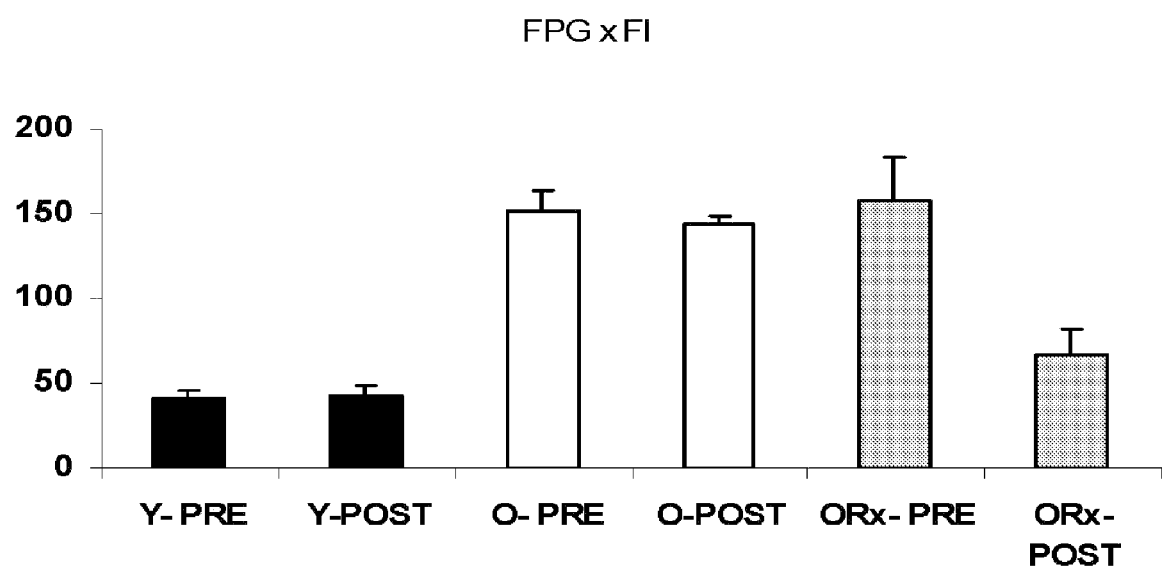
FIG. 34 demonstrates insulin response to GTT in the treated mice compared to controls. GTT is 'Glucose tolerance test' and the product of the fasting plasma glucose (FPG) and fasting insulin (FI) provides an index of insulin sensitivity.
Figure 35:
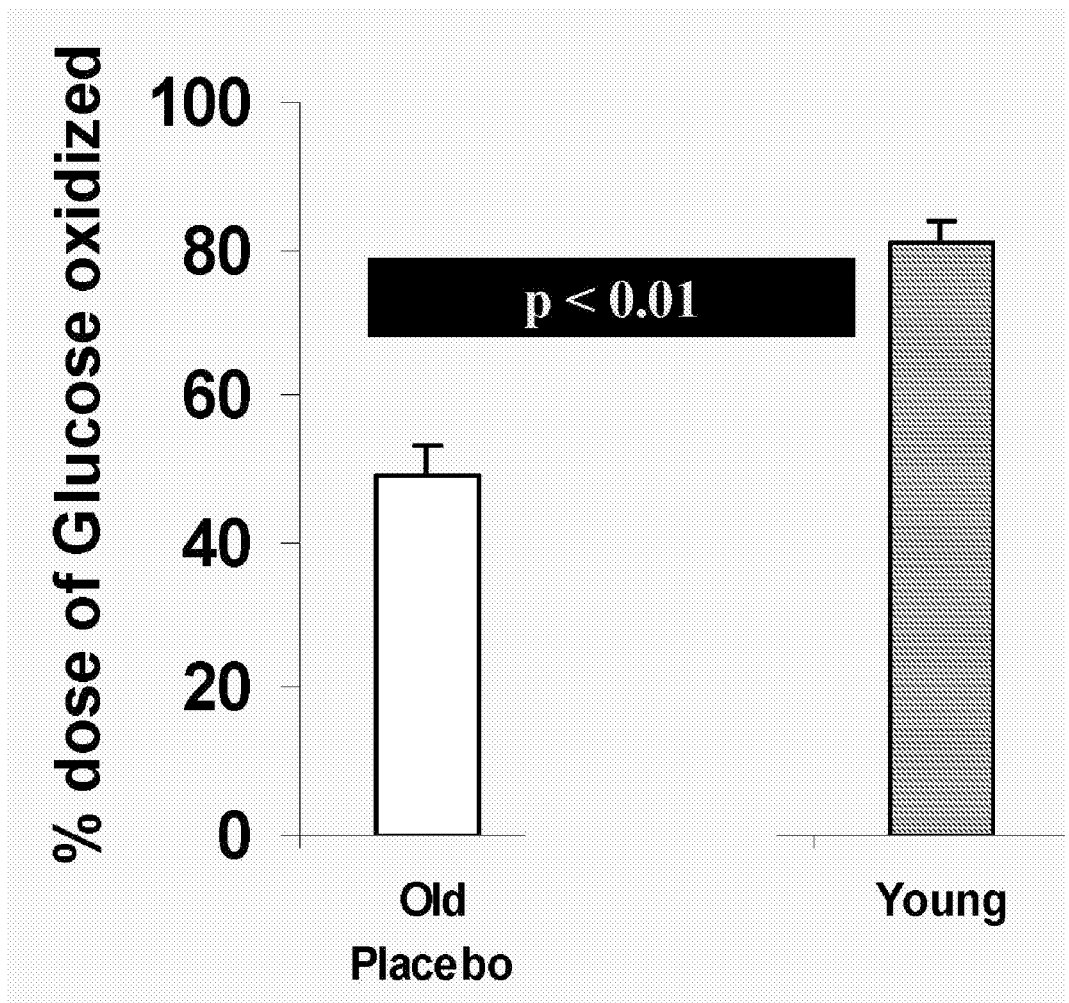
FIG. 35 shows $^{13}C_6$-glucose oxidation in young versus old mice.
Figure 36:
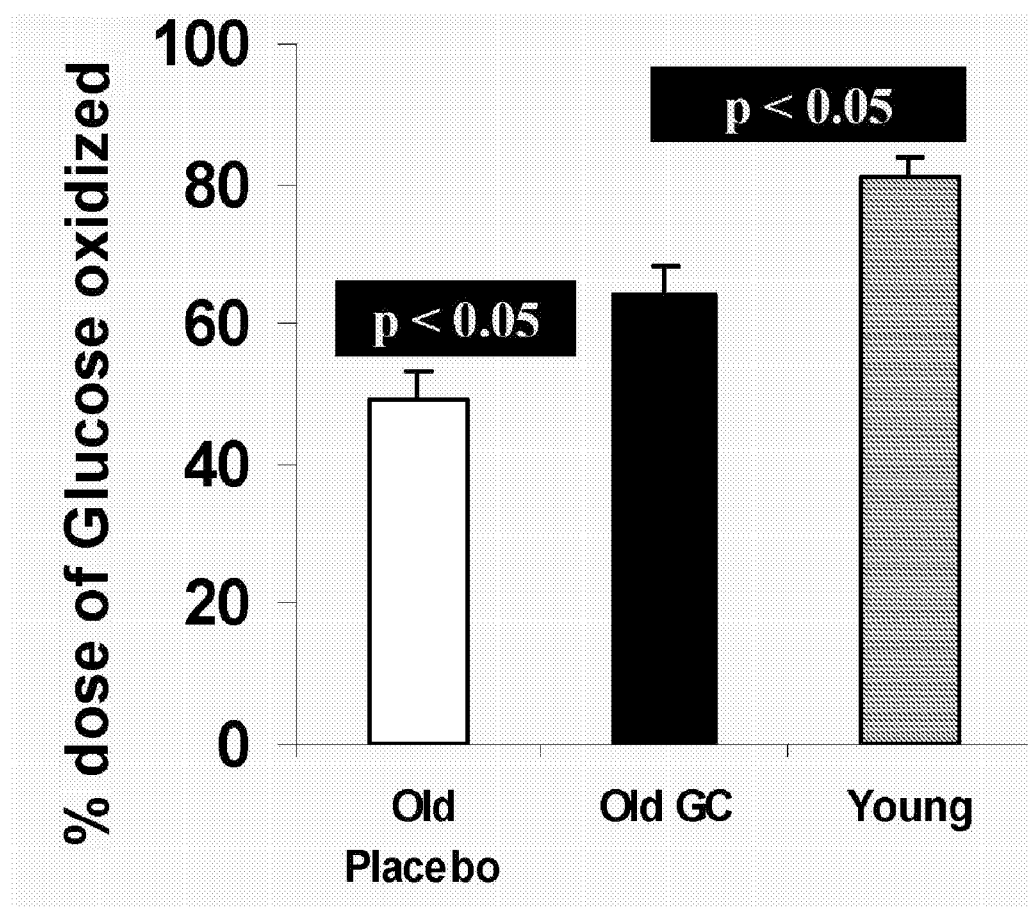
FIG. 36 shows $^{13}C_6$-glucose oxidation in treated old mice compared to young and untreated old mice.

In FIG. 34, treated old mice have a significantly improved insulin sensitivity (glucose-insulin product) compared to untreated old mice, and are similar to young mice following treatment. FIG. 35 shows $^{13}C_6$-glucose oxidation, including the oxidation of a labeled glucose as a direct measurement of fat oxidation; old mice have a significantly lower oxidation of glucose than young mice. In FIG. 36, treated old mice have a significantly higher oxidation of glucose than untreated old mice.

Figure 37:
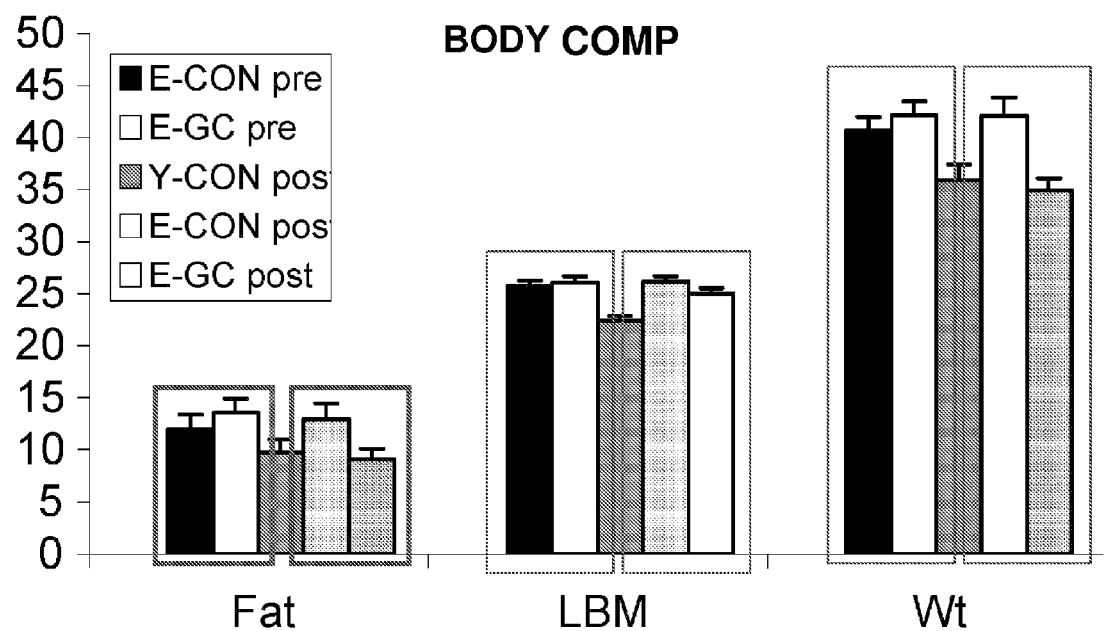
FIG. 37 shows body composition in treated versus control mice.

In FIG. 37, the Wt bars on the right show pre- and post-body weights in treated and untreated old mice and basal body weight in young mice. The treated old mice lose significant amount of weight compared to untreated old mice. The lean body mass (LBM) bars show pre- and post-LBM in treated and untreated old mice and basal LBM in young mice. There is no loss of lean body mass in the treated old mice, indicating that the loss in body weight must be due to loss of fat mass.

Figure 38:
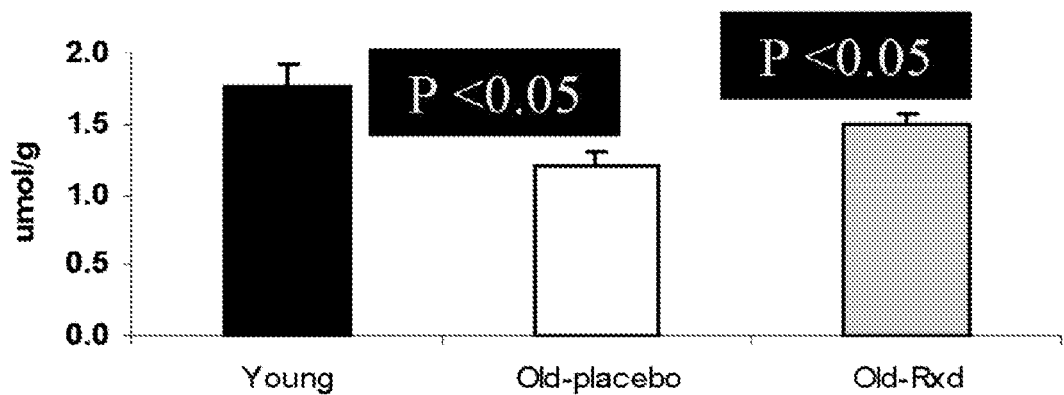
FIG. 38 shows GSH concentrations in liver and muscle of young, control old, and treated mice.
Figure 38:
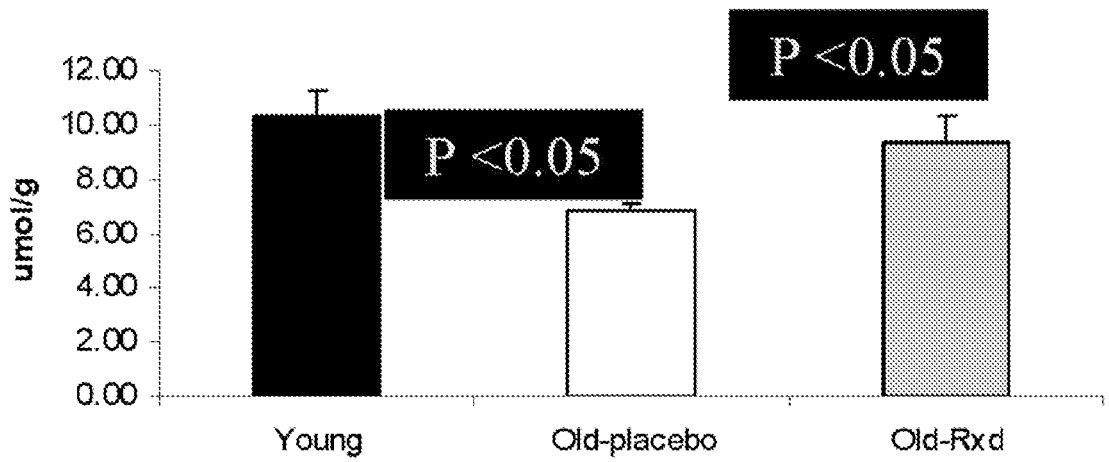

FIG. 38 shows GSH concentrations in liver and muscle of young, control old, and treated mice. Compared to young mice, the treated old mice (old-placebo group) have deficiency of glutathione concentrations in the liver and skeletal muscle of old mice. When supplemented with glycine and cysteine (as n-acetylcysteine) for 6 weeks, the treated old mice show a significant improvement of glutathione concentrations within the liver and skeletal muscle. Thus, the studies described herein show a reciprocal relation with GSH concentrations and fat oxidation with aging. Improving GSH concentrations with precursor supplementation results in improving dyslipidemia, insulin resistance and obesity in mice.

Figure 39:
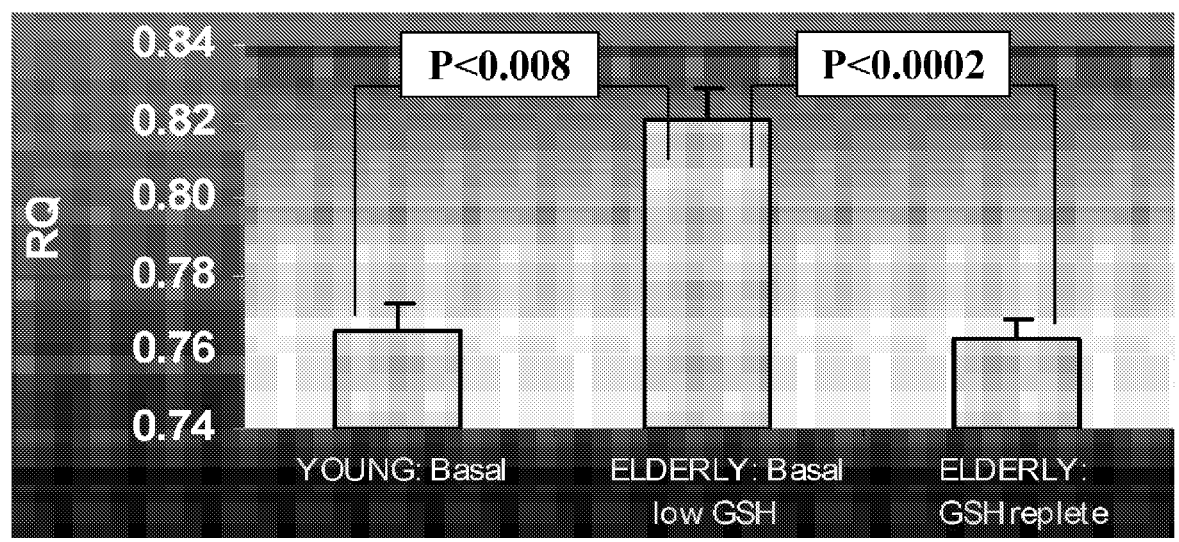
FIG. 39 shows respiratory quotient (RQ) in treated elderly humans compared to elderly controls and young controls.

FIG. 39 shows respiratory quotient (RQ) that is a measure that indirectly reflects which substrate is being used as fuel for generating energy. The graph shows that young humans in the fasted state have an RQ of 0.76, indicating that they are mainly burning fat to produce energy. Compared to young humans, the elderly humans in the fasted state have an RQ of 0.82, indicating that they are unable to burn fat to produce energy as well as young humans. After two weeks of dietary supplementation with glycine and cysteine (as n-acetylcysteine), elderly humans are able to significantly lower their RQ in the fasted state, indicating that they are now able to improve their ability to burn fat to produce energy.

Figure 40:
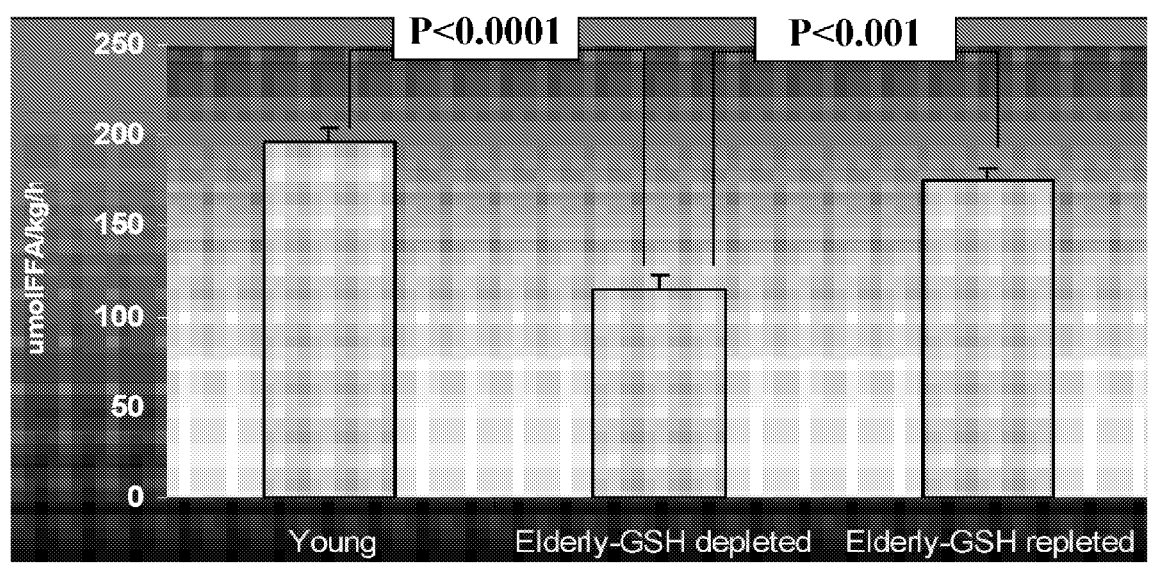
FIG. 40 demonstrates fat oxidation in young humans compared to elderly humans either treated with dietary supplementation of the invention or not treated.

FIG. 40 shows fat oxidation calculated from calorimetric data. In the basal state, after a prolonged fast, elderly humans are not able to oxidez fat as well as young humans. After 2 weeks of dietary supplementation with glycine and cysteine (as n-acetylcysteine) the same elderly humans are now able to significantly increase fat oxidation in the fasted state to that of young humans, indicating that the improved levels of glutathione is associated with an improved ability to oxidize fat to produce energy.

Figure 41:
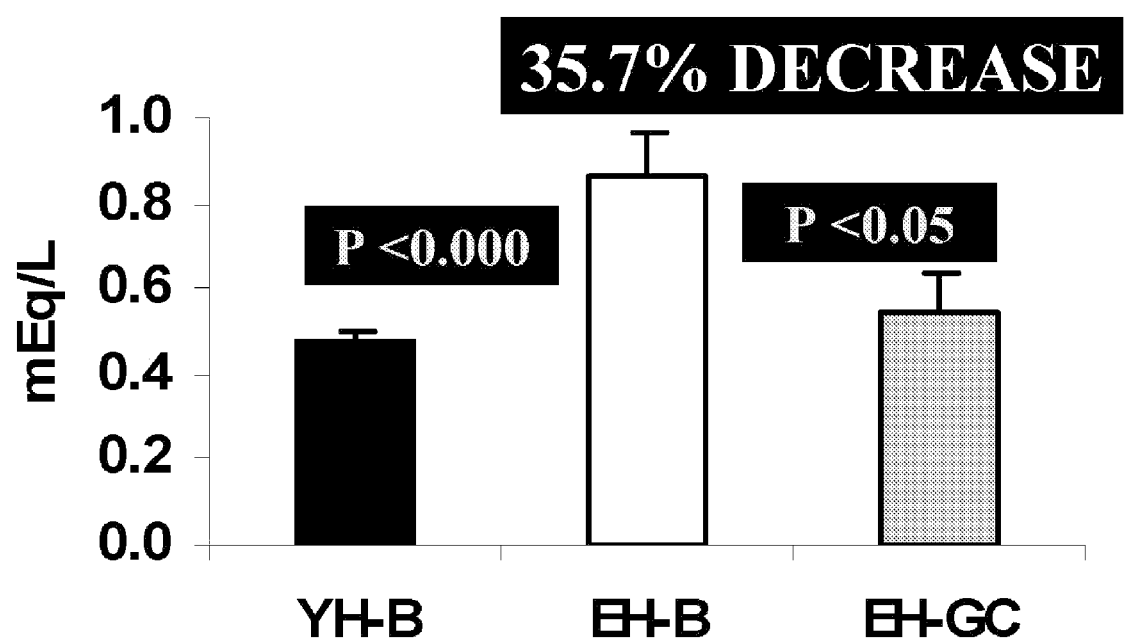
FIG. 41 shows fasting plasma fatty-acid concentrations in young humans, elderly untreated humans (EH-B) and elderly treated humans (EH-GC).

FIG. 41 shows fasting plasma fatty-acid concentrations in young and elderly. Compared to young humans, the elderly humans in the fasted state have a much higher concentration of fatty acids in the plasma. After increasing glutathione concentrations (with two weeks of supplementation with n-acetylcysteine and glycine), plasma fatty acid concentrations in elderly humans decreased by 35.7%.

Figure 26:
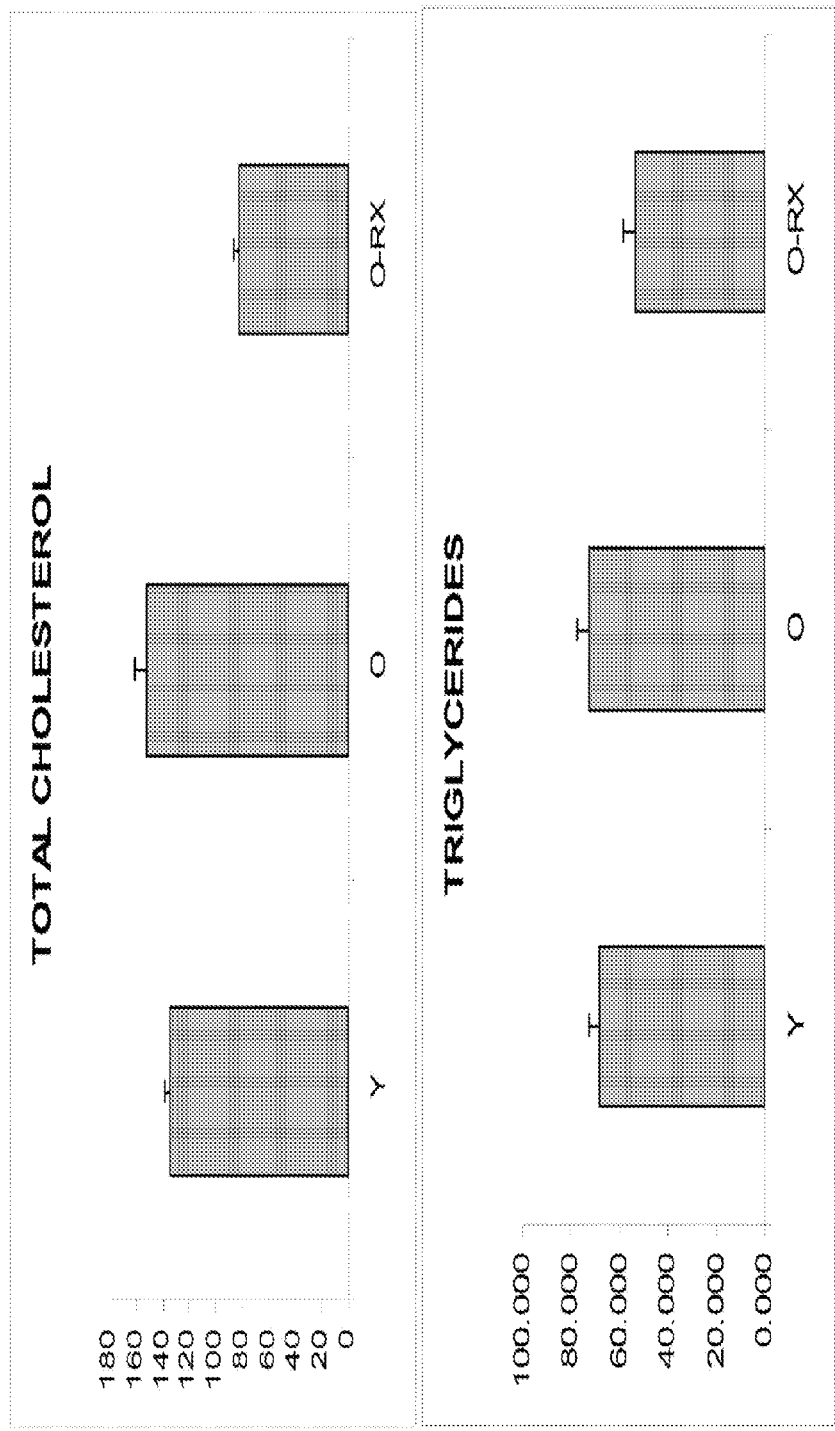
FIG. 26 shows that improving glutathione lowers total cholesterol and triglyceride levels in mice.

FIG. 26 shows that improving glutathione concentrations also lowers total cholesterol and triglyceride levels in old mice.

Figure 42:
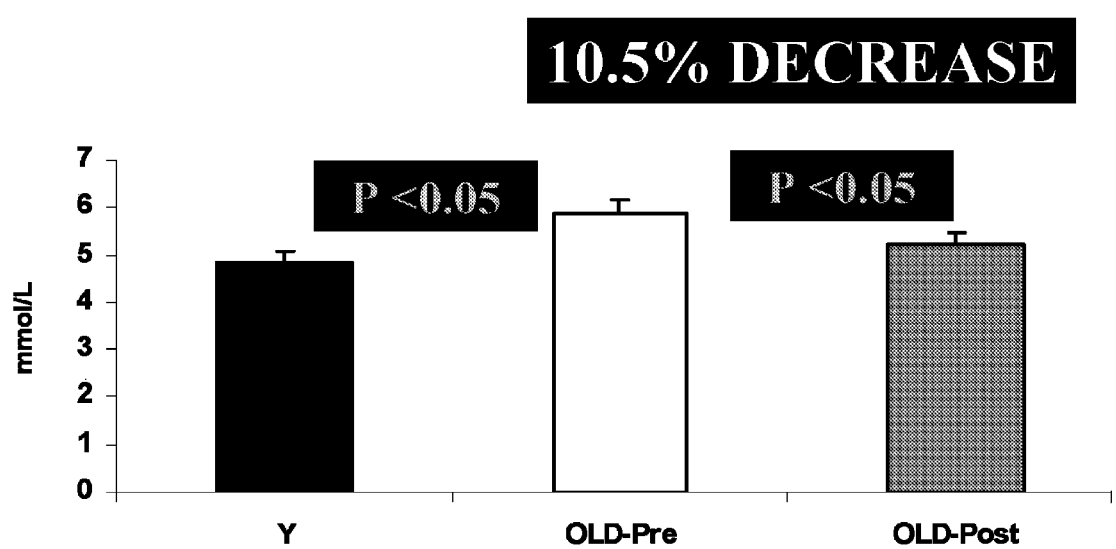
FIG. 42 shows fasting plasma glucose in young humans compared to treated and untreated elderly humans.

FIG. 42 shows fasting plasma glucose in elderly humans after increasing glutathione concentrations (with 2 weeks of supplementation with n-acetylcysteine and glycine); fasting plasma glucose concentrations in elderly humans decreased by 10.5%.

Therefore, these studies indicate that improving GSH concentrations with precursor supplementation is associated with improving fatty-acid oxidation and lowering fatty acid concentrations in humans. Improving oxidation of fatty acids with improvements in glutathione concentrations using glycine and n-acetylcysteine supplementation is useful to target obesity, dyslipidemia, insulin resistance and non-alcoholic fatty liver disease in humans, for example.

Example 10

Glutathione in Treatment of Fibromyalgia and Statin-Induced Myopathy

Figure 43:
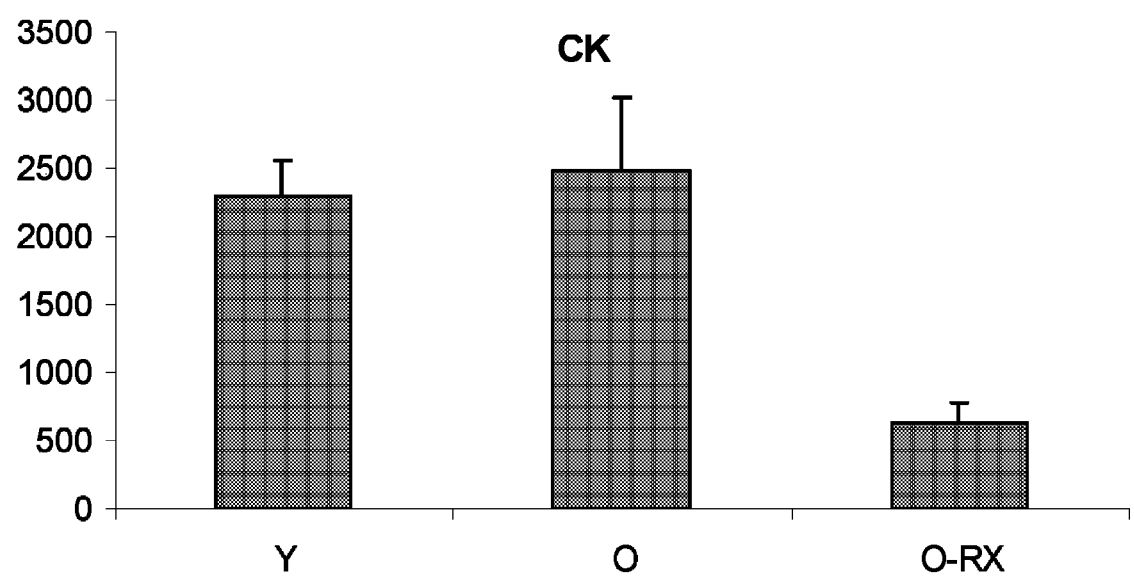
FIG. 43 shows plasma concentrations of creatine kinase in treated and untreated old mice, and young mice.

FIG. 43 shows plasma concentrations of creatine kinase, which is a biomarker of muscle damage. CK levels after 6 weeks of study are shown. Treated old mice shows significant lowering of CK compared to untreated old mice and young mice, indicating a beneficial effect of improving glutathione.

Example 11

Impaired Glutathione Turnover and Increased Oxidative Stress and Oxidant Damage in Uncontrolled Diabetes and the Beneficial Effects of Dietary Supplements with Glycine and N-Acetylcysteine This example shows impaired glutathione turnover and increased oxidative stress and oxidant damage in uncontrolled diabetes and the beneficial effects of dietary supplements with glycine and n-acetylcysteine. In an exemplary study, stable isotope infusions were used to study 12 diabetic and 12 healthy humans. The study measured GSH synthesis, erythrocyte GSH concentrations, plasma oxidative stress, and oxidant damage. Concentrations of 1.33 mmol/kg/d for glycine and 0.83 mmol/kg/d for NAC were delivered for 14 days, for example.

Figure 44:
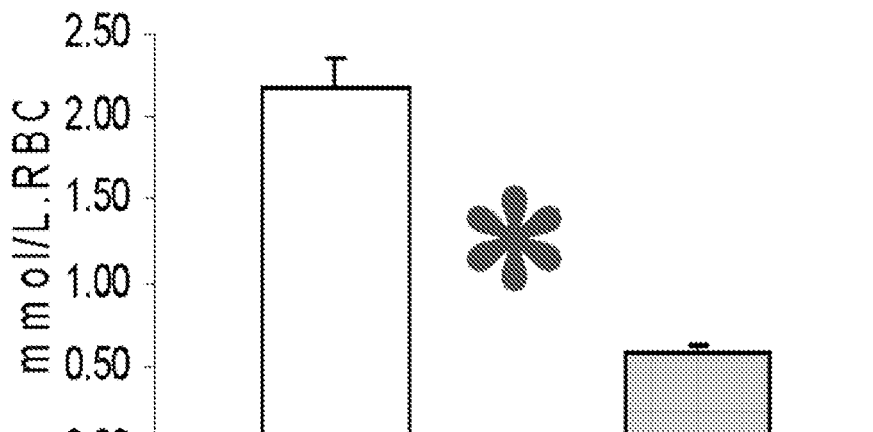
FIG. 44 demonstrates RBC glutathione concentrations in treated and untreated uncontrolled diabetics.
Figure 44:
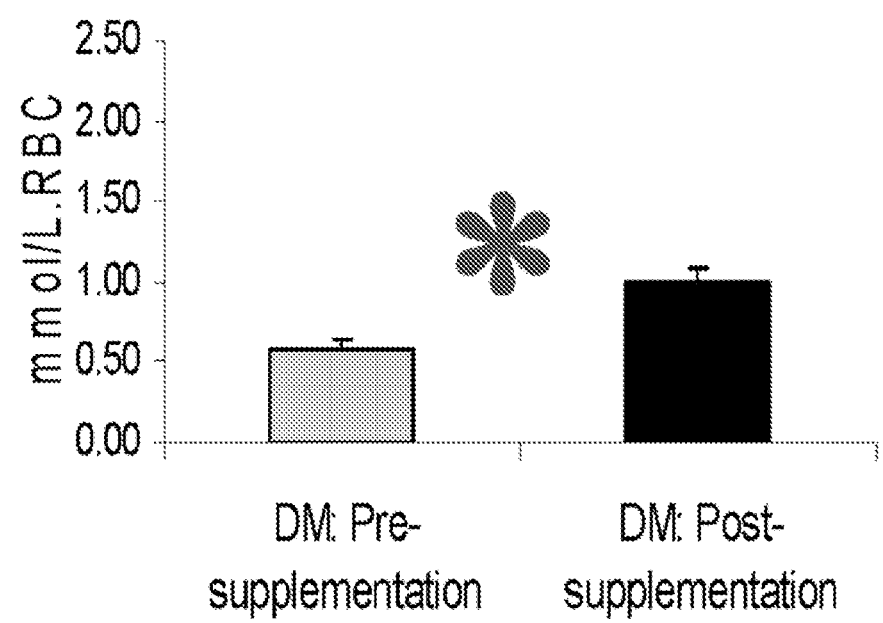
Figure 45:
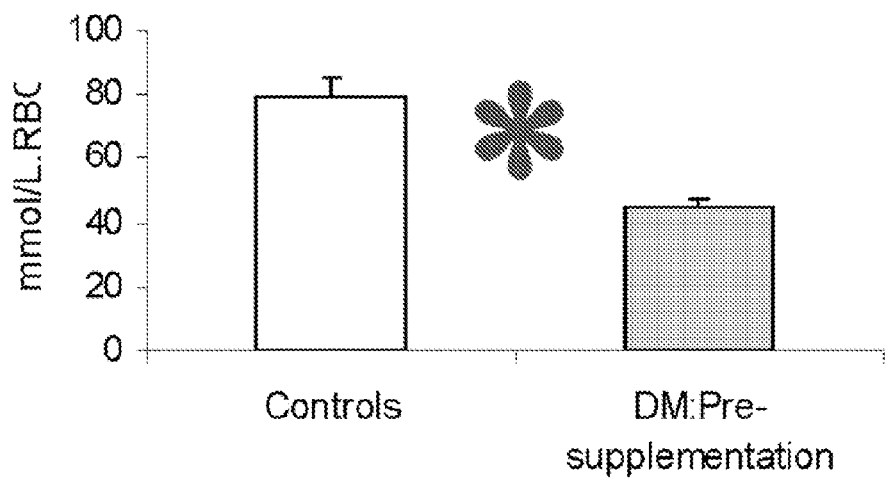
FIG. 45 shows GSH fractional synthesis rate in treated and untreated uncontrolled diabetics.
Figure 45:
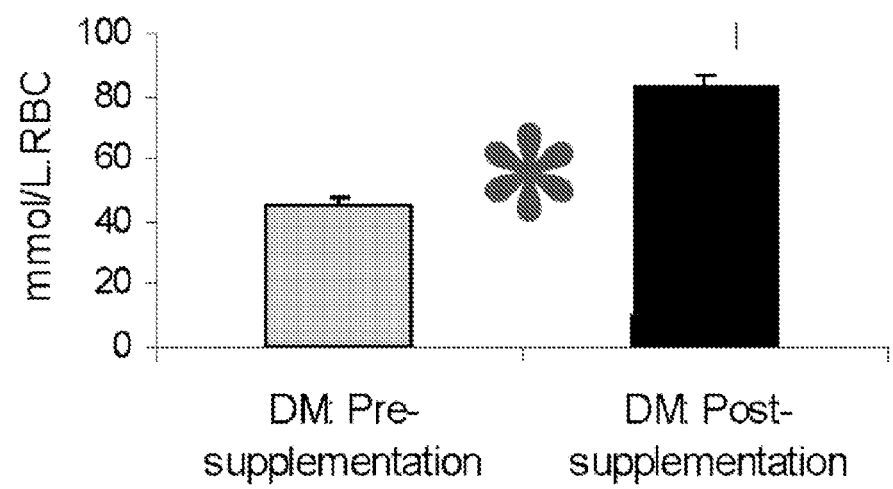

FIG. 44 shows red blood cell glutathione concentrations. In the left panel, compared to nondiabetic humans, humans with uncontrolled diabetes have deficiency of glutathione, a key antioxidant. In the right panel, providing dietary supplementation of cysteine (as n-acetylcysteine) and glycine in the diet significantly increases concentrations in humans with uncontrolled diabetes. FIG. 45 shows GSH fractional synthesis rate. In the left panel, glutathione deficiency in humans with uncontrolled diabetes occurs because of decreased synthesis. In the right panel, providing dietary supplementation of cysteine (as n-acetylcysteine) and glycine in the diet significantly increased glutathione synthesis and therefore the concentrations in severely diabetic humans. Glutathione synthesis rates were measured by the incorporation of labeled glycine into glutathione, by using stable isotope tracers and gas chromatography/mass spectrometry.

FIG. 46 concerns oxidative stress and oxidant damage. Lipid peroxides (LPO) are biomarkers of oxidant damage, and DROMs are biomarkers of oxidative stress. Compares to nondiabetic humans, humans with uncontrolled diabetes had increased LPO and DROMs in the glutathione deficient state indicating that there is increased damage due to oxidative stress. When glutathione synthesis and concentrations were corrected with dietary supplementation of cysteine (as n-acetylcysteine) and glycine, the levels of these markers fell significantly in diabetic humans, indicating that there was a significant decrease in diabetic damage even though there was no decrease in the severely elevated blood glucose levels.

Therefore, humans with poorly controlled diabetes have decreased GSH levels because of diminished synthesis; synthesis is decreased due to poor availability of precursor amino acids. The low GSH state predisposes one to increased oxidative stress, as measured by plasma markers of oxidative damage. Dietary supplementation with both NAC and glycine results in improved GSH synthesis and concentrations, and lowers oxidative stress and plasma markers of damage.

Example 12

Figure 47:
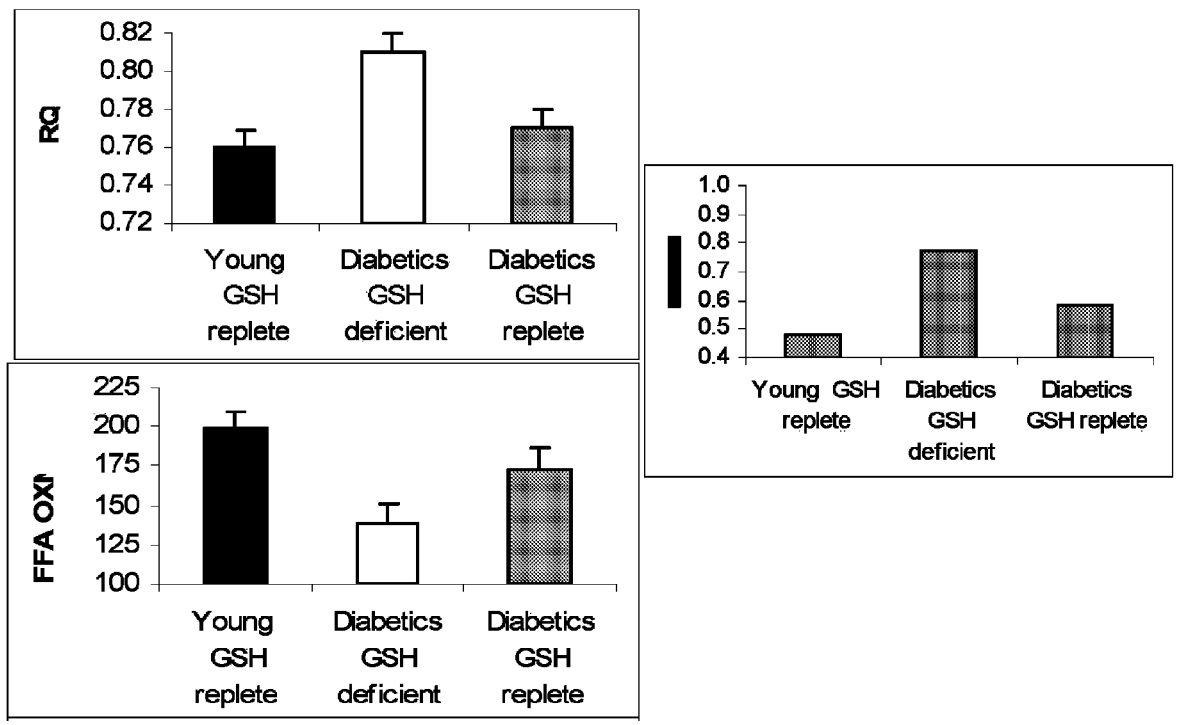
FIG. 47 shows improving GSH also results in increasing fat oxidation and decreasing fatty acid concentrations in humans with uncontrolled diabetes.

Glutathione in Treatment of Impaired Fatty Acid Oxidation in Humans with Uncontrolled Diabetes FIG. 47 shows improving GSH also results in increasing fat oxidation and decreasing fatty acid concentrations in humans with uncontrolled diabetes.

Example 13

Diabetic Mice: Energy Metabolism

Figure 48:
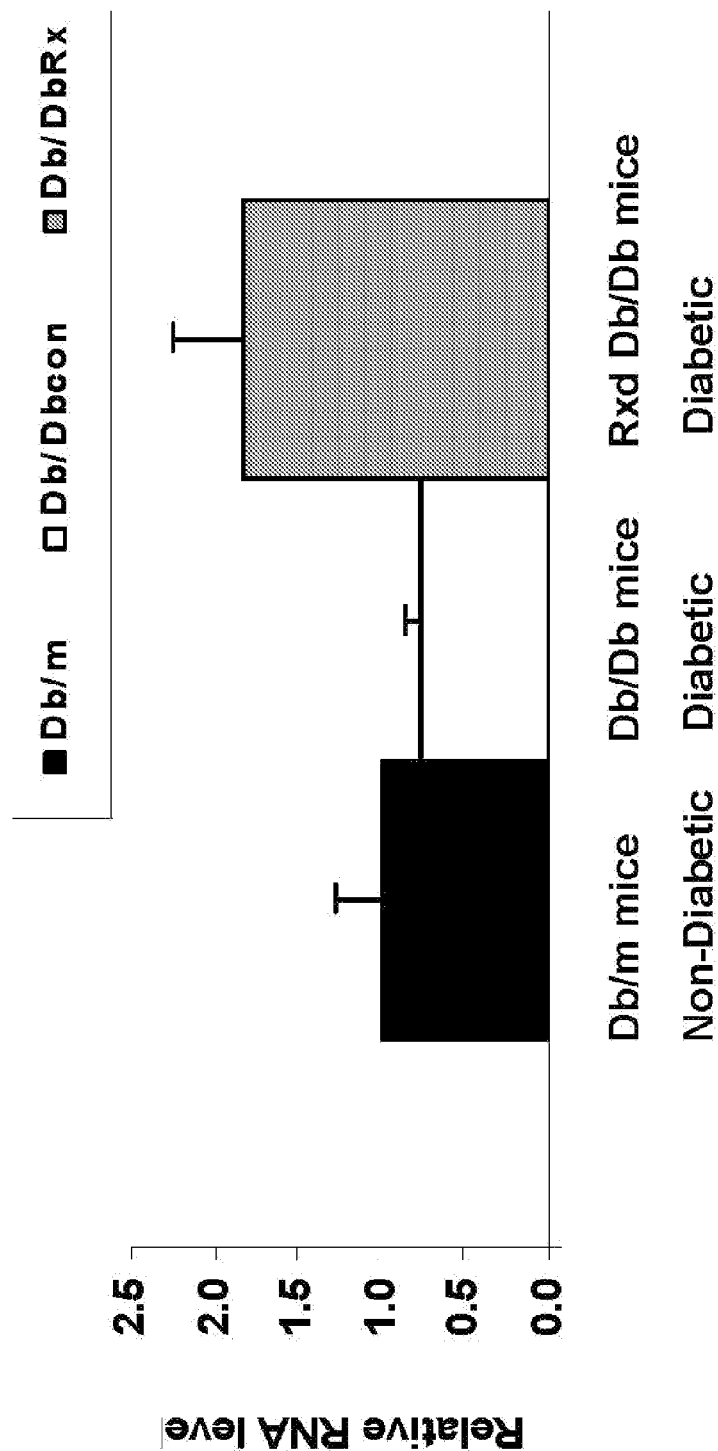
FIG. 48 shows energy metabolism in diabetic mice.

Untreated db/db mice (unsupplemented) have lower PGC1a than nondiabetic mice. After 6 weeks of glycine+ cysteine supplementation in the db/db mice, PGC1a increases, indicating that there are beneficial effects on mitochondrial biogenesis/function and fatty acid oxidation (FIG. 48).

Thus, improving GSH concentrations with precursor supplementation is associated with improving fatty-acid oxidation and lowering fatty acid concentrations in humans. Improving oxidation of fatty acids with improvements in glutathione concentrations using glycine and n-acetylcysteine supplementation is useful to target non-alcoholic fatty liver disease in diabetic humans.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

PUBLICATIONS

Al-Turk W A, Stohs S J, el-Rashidy F H, Othman S. Changes in glutathione and its metabolizing enzymes in human erythrocytes and lymphocytes with age. J Pharm Pharmacol 1987; 39:13-6.

Bella D L, Hahn C, Stipanuk M H. Effects of nonsulfur and sulfur amino acids on the regulation of hepatic enzymes of cysteine metabolism. Am J Physiol 1999; 277:E144-53.

Boirie Y, Gachon P, Beaufrere B. Splanchnic and whole-body leucine kinetics in young and elderly men. Am J Clin Nutr 1997; 65:489-95.

Campisi A, Di Giacomo C, Russo A, et al. Antioxidant systems in rat lens as a function of age: effect of chronic administration of vitamin E and ascorbate. Aging (Milano) 1999; 11:39-43.

Campbell W W, Crim M C, Dallal G E, Young V R, Evans W J. Increased protein requirements in elderly people: new data and retrospective reassessments. Am J Clin Nutr 1994; 60:501-9.

Castorina C, Campisi A, Di Giacomo C, Sorrenti V, Russo A, Vanella A. Lipid peroxidation and antioxidant enzymatic systems in rat retina as a function of age. Neurochem Res 1992; 17:599-604.

Cresenzi C L, Lee J I, Stipanuk M H. Cysteine is the metabolic signal responsible for dietary regulation of hepatic cysteine dioxygenase and glutamate cysteine ligase in intact rats. J Nutr 2003; 133:2697-702.

Erden-Inal M, Sunal E, Kanbak G. Age-related changes in the glutathione redox system. Cell Biochem Funct 2002; 20:61-6.

Farooqui M Y, Day W W, Zamorano D M. Glutathione and lipid peroxidation in the aging rat. Comp Biochem Physiol B 1987; 88:177-80.

Fereday A, Gibson N R, Cox M, Pacy P J, Millward D J. Protein requirements and ageing: metabolic demand and efficiency of utilization. Br J Nutr 1997; 77:685-702.

Fidelus R K, Tsan M F. Glutathione and lymphocyte activation: a function of ageing and auto-immune disease. Immunology 1987; 61:503-8.

Furukawa T, Meydani S N, Blumberg J B. Reversal of age-associated decline in immune responsiveness by dietary glutathione supplementation in mice. Mech Ageing Dev 1987; 38:107-17.

Grimble R F, Jackson A A, Persaud C, Wride M J, Delers F, Engler R. Cysteine and glycine supplementation modulate the metabolic response to tumor necrosis factor alpha in rats fed a low protein diet. J Nutr 1992; 122:2066-73.

Hashimoto K, Takasaki W, Yamoto T, Manabe S, Sato I, Tsuda S. Effect of glutathione (GSH) depletion on DNA damage and blood chemistry in aged and young rats. J Toxicol Sci 2008; 33:421-9.

Jackson A A, Gibson N R, Lu Y, Jahoor F. Synthesis of erythrocyte glutathione in healthy adults consuming the safe amount of dietary protein. Am J Clin Nutr 2004; 80:101-7.

Jahoor F, Wykes L J, Reeds P J, Henry J F, del Rosario M P, Frazer M E. Protein-deficient pigs cannot maintain reduced glutathione homeostasis when subjected to the stress of inflammation. J Nutr 1995; 125:1462-72.

Lang C A, Naryshkin S, Schneider D L, Mills B J, Lindeman R D. Low blood glutathione levels in healthy aging adults. J Lab Clin Med 1992; 120:720-5.

Liu R, Choi J. Age-associated decline in gamma-glutamyl-cysteine synthetase gene expression in rats. Free Radic Biol Med 2000; 28:566-74.

Liu H, Wang H, Shenvi S, Hagen T M, Liu R M. Glutathione metabolism during aging and in Alzheimer disease. Ann N Y Acad Sci 2004; 1019:346-9.

Loguercio C, Taranto D, Vitale L M, Beneduce F, Del Vecchio Blanco C. Effect of liver cirrhosis and age on the glutathione concentration in the plasma, erythrocytes, and gastric mucosa of man. Free Radic Biol Med 1996; 20:483-8.

Lyons J, Rauh-Pfeiffer A, Yu Y M, et al. Blood glutathione synthesis rates in healthy adults receiving a sulfur amino acid-free diet. Proc Natl Acad Sci USA 2000; 97:5071-6.

Matsubara L S, Machado P E. Age-related changes of glutathione content, glutathione reductase and glutathione peroxidase activity of human erythrocytes. Braz J Med Biol Res 1991; 24:449-54.

Morais J A, Gougeon R, Pencharz P B, Jones P J, Ross R, Marliss E B. Whole-body protein turnover in the healthy elderly. Am J Clin Nutr 1997; 66:880-9.

Rebrin I, Sohal R S. Pro-oxidant shift in glutathione redox state during aging. Adv Drug Deliv Rev 2008; 60:1545-52.

Reid M, Jahoor F. Methods for measuring glutathione concentration and rate of synthesis. Curr Opin Clin Nutr Metab Care 2000; 3:385-90.

Rikans L E, Hornbrook K R. Lipid peroxidation, antioxidant protection and aging. Biochim Biophys Acta 1997; 1362:116-27.

Rizvi S I, Maurya P K. Markers of oxidative stress in erythrocytes during aging in humans. Ann N Y Acad Sci 2007; 1100:373-82.

Samiec P S, Drews-Botsch C, Flagg E W, et al. Glutathione in human plasma: decline in association with aging, age-related macular degeneration, and diabetes. Free Radic Biol Med 1998; 24:699-704.

Stohs S J, Lawson T, Al-Turk W A. Changes in glutathione and glutathione metabolizing enzymes in erythrocytes and lymphocytes of mice as a function of age. Gen Pharmacol 1984; 15:267-70.

Sweeney M H, Truscott R J. An impediment to glutathione diffusion in older normal human lenses: a possible precondition for nuclear cataract. Exp Eye Res 1998; 67:587-95.

Toroser D, Sohal R S. Age-associated perturbations in glutathione synthesis in mouse liver. Biochem J 2007; 405: 583-9.

Young V R. Amino acids and proteins in relation to the nutrition of elderly people. Age Ageing 1990; 19:S10-24.

Although the present invention and its advantages have been described in detail, it should be understood that various changes, substitutions and alterations can be made herein without departing from the invention as defined by the claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the claims are intended to include within their scope such processes, machines, manufacture, compositions of matter, means, methods, or steps.

The claimed invention is:

1. A method of preventing diabetes in an individual in need thereof, comprising the step of providing an effective amount of glycine and n-acetylcysteine to the individual.

2. The method of claim 1, wherein the glycine and n-acetylcysteine are provided to the individual in the same composition.

3. The method of claim 1, wherein the glycine and n-acetylcysteine are provided orally to the individual.

4. A method of treating and/or preventing a medical condition selected from diabetes or complications of diabetes in an individual in need thereof, wherein the medical condition is associated with reduced glutathione levels, comprising the steps of:
   a) identifying an individual in need of treatment of the medical condition; and
   b) providing an effective amount of glycine and N-acetylcysteine to the individual.

5. A method of increasing GSH levels in an individual in need thereof, comprising the step of providing an effective amount of glycine and n-acetylcysteine to the individual, wherein the individual in need thereof is at least sixty years of age and/or has diabetes.

6. A method of reducing body weight, lowering cholesterol level, and/or lowering triglyceride level in an individual, comprising the step of providing an effective amount of glycine and n-acetylcysteine to the individual.

* * * * *